US010504670B2

(12) United States Patent
Sundaresan et al.

(10) Patent No.: US 10,504,670 B2
(45) Date of Patent: Dec. 10, 2019

(54) KEYCAP WITH AN ACTIVE ELEMENT

(71) Applicant: Intel Corporation, Santa Clara, CA (US)

(72) Inventors: Sukanya Sundaresan, Karnataka (IN); Reji Varghese, Bangalore (IN); Ramesh Pendakur, Bangalore (IN); Ayeshwarya B. Mahajan, Bangalore (IN)

(73) Assignee: Intel Corporation, Santa Clara, CA (US)

( * ) Notice: Subject to any disclaimer, the term of this patent is extended or adjusted under 35 U.S.C. 154(b) by 0 days.

(21) Appl. No.: 15/749,483

(22) PCT Filed: Apr. 2, 2016

(86) PCT No.: PCT/US2016/025768
§ 371 (c)(1),
(2) Date: Jan. 31, 2018

(87) PCT Pub. No.: WO2017/023372
PCT Pub. Date: Feb. 9, 2017

(65) Prior Publication Data
US 2018/0233307 A1 Aug. 16, 2018

(30) Foreign Application Priority Data

Jul. 31, 2015 (IN) .......................... 3958/CHE/2015
Jul. 31, 2015 (IN) .......................... 3959/CHE/2015
Jul. 31, 2015 (IN) .......................... 3961/CHE/2015

(51) Int. Cl.
H01H 13/83 (2006.01)
H01H 13/79 (2006.01)
(Continued)

(52) U.S. Cl.
CPC ........... *H01H 13/83* (2013.01); *A61B 5/0402* (2013.01); *A61B 5/0537* (2013.01);
(Continued)

(58) Field of Classification Search
CPC .... H01H 13/83; H01H 13/704; H01H 13/705; H01H 2219/02; G06F 3/0233
See application file for complete search history.

(56) References Cited

U.S. PATENT DOCUMENTS 4,551,717 A 11/1985 Dreher
4,853,888 A 8/1989 Lata et al.
(Continued)

FOREIGN PATENT DOCUMENTS

JP 2004184945 A 7/2004
JP 2008250259 A 10/2008
(Continued)

OTHER PUBLICATIONS

International Search Report and Written Opinion in International Patent Application No. PCT/US2016/025767 dated Jul. 20, 2016, 9 pages).
(Continued)

Primary Examiner — Amine Benlagsir
(74) Attorney, Agent, or Firm — Patent Capital Group

(57) ABSTRACT

Particular embodiments described herein provide a display that includes a mask that includes a one or more exposed areas, a top electrode, one or more bottom electrodes, a dielectric between the top electrode and the one or more bottom electrodes, and an electrical connection to create a differential voltage between the top electrode and the one or more bottom electrodes.

18 Claims, 19 Drawing Sheets

(51) Int. Cl.
  *A61B 5/0402* (2006.01)
  *A61B 5/053* (2006.01)
  *A61B 5/00* (2006.01)
  *G06F 3/023* (2006.01)
  *H01H 13/705* (2006.01)
  *H01H 3/12* (2006.01)
  *H01H 13/704* (2006.01)
  *H01H 13/7065* (2006.01)

(52) U.S. Cl.
  CPC .......... *A61B 5/6897* (2013.01); *A61B 5/6898* (2013.01); *G06F 3/0233* (2013.01); *G06F 3/0238* (2013.01); *H01H 13/705* (2013.01); *H01H 13/79* (2013.01); *H01H 3/125* (2013.01); *H01H 13/704* (2013.01); *H01H 13/7065* (2013.01); *H01H 2203/038* (2013.01); *H01H 2219/002* (2013.01); *H01H 2219/01* (2013.01); *H01H 2219/012* (2013.01); *H01H 2219/02* (2013.01); *H01H 2227/026* (2013.01)

(56) References Cited

U.S. PATENT DOCUMENTS

| | | | |
|---|---|---|---|
| 6,704,004 B1* | 3/2004 | Ostergård | H01H 13/83 178/18.11 |
| 6,797,902 B2* | 9/2004 | Farage | G06F 3/0202 200/314 |
| 6,798,359 B1 | 9/2004 | Ivancic | |
| 8,350,728 B2 | 1/2013 | Liu et al. | |
| 2002/0022113 A1 | 2/2002 | Kimura | |
| 2003/0058223 A1 | 3/2003 | Tracy et al. | |
| 2004/0217939 A1 | 11/2004 | Levy et al. | |
| 2006/0179088 A1 | 8/2006 | Kang | |
| 2008/0011596 A1 | 1/2008 | Lee et al. | |
| 2008/0024425 A1* | 1/2008 | Shido | G02F 1/167 345/107 |
| 2008/0179173 A1* | 7/2008 | Jung | H01H 13/83 200/314 |
| 2011/0056814 A1* | 3/2011 | Cheng | H01H 9/182 200/310 |
| 2011/0148766 A1 | 6/2011 | Huang | |
| 2013/0076634 A1 | 3/2013 | Pedersen et al. | |
| 2014/0028564 A1* | 1/2014 | Valentine | G06F 1/1662 345/168 |
| 2015/0084871 A1 | 3/2015 | Yarvis et al. | |
| 2016/0157781 A1 | 6/2016 | Baxi et al. | |
| 2018/0158625 A1 | 6/2018 | Mahajan et al. | |
| 2018/0226210 A1 | 8/2018 | Varghese et al. | |

FOREIGN PATENT DOCUMENTS

| | | |
|---|---|---|
| KR | 20110068209 A | 6/2011 |
| WO | 2008066490 A1 | 6/2008 |
| WO | 2017023371 A1 | 2/2017 |
| WO | 2017023372 A1 | 2/2017 |

OTHER PUBLICATIONS

International Search Report and Written Opinion in International Patent Application No. PCT/US2016/025768 dated Jul. 12, 2016, 9 pages).
USPTO Nov. 15, 2018 Notice of Allowance from U.S. Appl. No. 15/716,554 dated Nov. 15, 2018; 6 pages.
USPTO Feb. 21, 2019 Notice of Allowance issued in U.S. Appl. No. 15/749,393 (17 pages).
PCT Feb. 15, 2018 International Preliminary Report on Patentability issued in PCT/US2016/025767 dated Feb. 15, 2018; 8 pages.
USPTO Jul. 11, 2018 Non-Final Office Action issued in U.S. Appl. No. 15/716,554 dated Jul. 11, 2018 (10 pages).
USPTO Oct. 4, 2018 Non-Final Office Action issued in U.S. Appl. No. 15/749,393 dated Oct. 4, 2018 (16 pages).

* cited by examiner

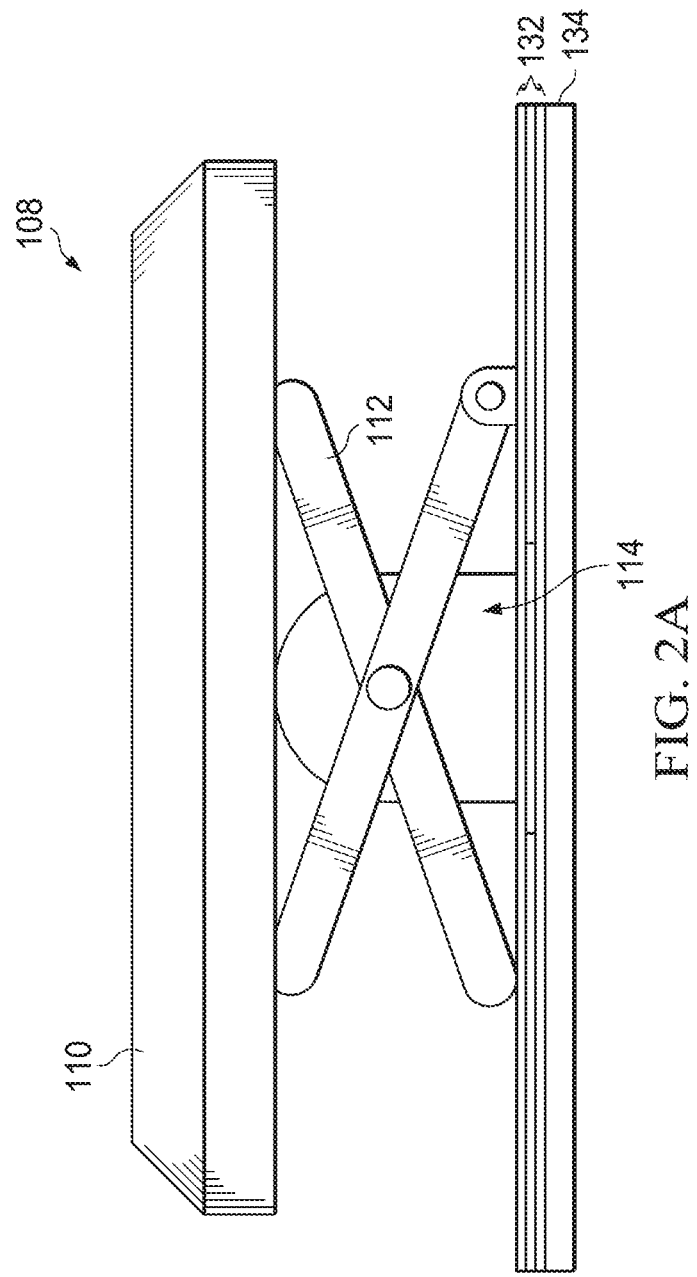

KEYCAP WITH AN ACTIVE ELEMENT

CROSS-REFERENCE TO RELATED APPLICATIONS

This Application is a national stage application under 35 U.S.C. § 371 of PCT Application PCT/US2016/025768, filed Apr. 2, 2016 and entitled "KEYCAP WITH AN ACTIVE ELEMENT", which claims priority to Provisional Application No. 3958/CHE/2015, entitled "BI-STABLE DISPLAY" filed in the Indian Patent Office on Jul. 31, 2015, to Provisional Application No. 3961/CHE/2015, entitled "KEYBOARD WITH DISPLAY EMBEDDED KEYS AND DEVICE TO SENSE BIO-SIGNALS" filed in the Indian Patent Office on Jul. 31, 2015, and to Provisional Application No. 3959/CHE/2015, entitled "KEYCAP WITH ACTIVE ELEMENTS" filed in the Indian Patent Office on Jul. 31, 2015, which are hereby incorporated by reference in their entirety.

TECHNICAL FIELD

This disclosure relates in general to the field of electronic devices, and more particularly, to a keycap with an active element.

BRIEF DESCRIPTION OF THE DRAWINGS

To provide a more complete understanding of the present disclosure and features and advantages thereof, reference is made to the following description, taken in conjunction with the accompanying FIGURES, embodiments are illustrated by way of example and not by way of limitation in the FIGURES of the accompanying drawings, in which like references indicate similar elements and in which:

FIG. 2A is a simplified schematic diagram illustrating a plan view of an embodiment of a portion of a keyboard, in accordance with one embodiment of the present disclosure;

The FIGURES of the drawings are not necessarily drawn to scale, as their dimensions can be varied considerably without departing from the scope of the present disclosure.

DETAILED DESCRIPTION OF EXAMPLE EMBODIMENTS

Example Embodiments

Figure 1A:
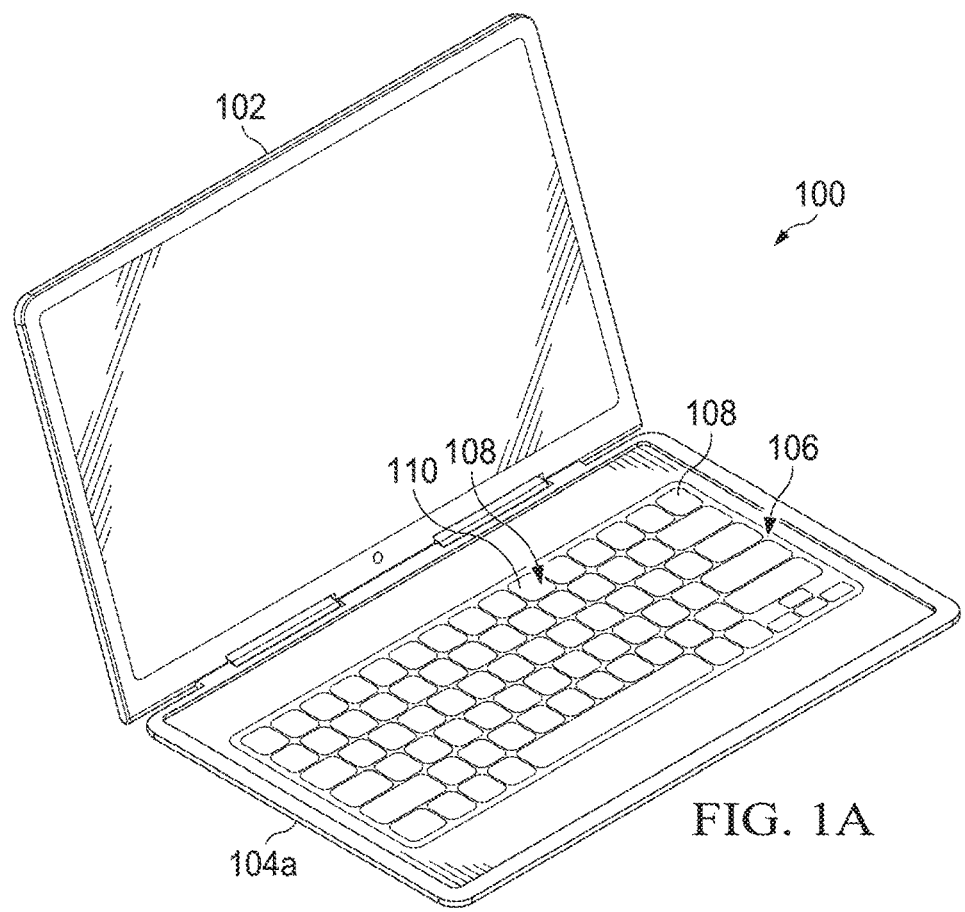
FIG. 1A is a simplified schematic diagram illustrating a perspective view of an embodiment of an electronic device, in accordance with one embodiment of the present disclosure.

FIG. 1A is a simplified schematic diagram illustrating an embodiment of an electronic device 100 in accordance with one embodiment of the present disclosure. Electronic device 100 can include a first housing 102 and a second housing 104a. Second housing 104a can include a keyboard portion 106. Keyboard portion 106 can include a plurality of keys 108 and each key 108 can include a keycap 110. In one or more embodiments, electronic device 100 may be any suitable electronic device having a keyboard or keys such as a computer that includes keys, a desktop computer, a mobile device that includes keys, a tablet device that includes keys, a Phablet™ that includes keys, a personal digital assistant (PDA) that includes keys, an audio system that includes keys, a movie player of any type that includes keys, etc.

Figure 1B:
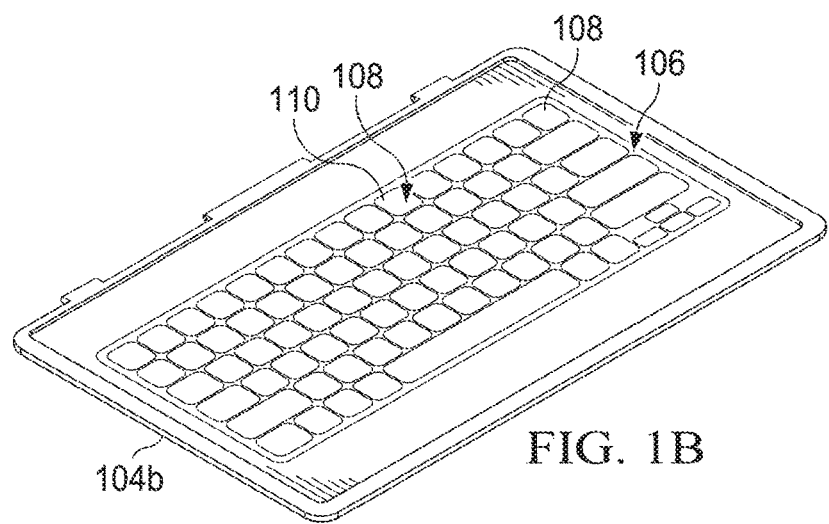
FIG. 1B is a simplified schematic diagram illustrating a perspective view of an embodiment of an electronic device, in accordance with one embodiment of the present disclosure.

Turning to FIG. 1B, FIG. 1B is a simplified schematic diagram of a detachable second housing 104b in accordance with one embodiment of the present disclosure. Detachable second housing 104b can include keyboard portion 106 and plurality of keys 108. Each key 108 can include a keycap 110. Second housing 104b may be a keyboard in communication with an electronic device (e.g., a standalone keyboard or Bluetooth™ keyboard in wireless communication with a smartphone, a desktop keyboard connected to a computer through a wire or cable) or may be physically attached to an electronic device (e.g. a keyboard integrated into the chassis of an electronic device).

For purposes of illustrating certain example features of a keycap with an active element, the following foundational information may be viewed as a basis from which the present disclosure may be properly explained. A tactile keyboard is mechanical keyboard where keys travel down when a user applies a force to press the keys and the keys strikes back to its original position after the user applied force is released. Such keyboards are used for data input in variety of applications such as laptops, desktop keyboards, industrial control systems, remote controls, automotive and many others etc. Tactile keyboards typically consist of different functional elements or blocks, such as a key, a dome, scissor, switch, and base plate. The dome can be a rubber, plastic, silicone, or metallic dome or any other similar element which is compressed and deforms when force is applied and rebounds back to its original shape and size when the applied force is removed. The scissor can be a scissor or any other similar element to lock the key and constrain its motion to only in the vertical direction. The switch is some form of switch which is closed when the key is pressed (to detect the input). The base plate can be a base plate or any other similar element which acts as a foundation for components of the keyboard.

A keycap of a keyboard is a small mechanical component which travels up and down when the key is pressed by a user. A typical keycap includes a fine curved surface on the top to provide ergonomic comfort when a finger of a user rests on the keycap. The typical keycap also includes a fine textured surface to prevent a glossy/shining finish and provide a subtle grip for the finger of the user when the finger presses the key. Some keycaps include a label (either printed or etched) on a topmost surface of the keycap to provide a wide angle of view (almost 180 degree) and allow identification of the key. In addition, the typical keycap can include a locking mechanism on the bottom side to provide mechanical (usually a snap fit) connection with rest of the keyboard subsystem. The thickness of the keycap at a periphery and at the locking mechanism is usually around 2 mm while the thickness in other areas is often around 1 mm. Most keycaps are designed to withstand multi-million operations.

Keyboards have traditionally remained passive mechanical devices for gathering user input. The focus on keyboards has generally been on the on mechanical aspects in making the keyboards thinner, quieter, with lower operating pressure, etc. The key is typically a passive component of the keyboard because there is not an electrical connection available at the key. Some keys do have an electrical connection but the electrical connection using existing methods (e.g., wires, cables, or pogo pins) have serious limitations as there is typically not enough space for the electrical connection. For example, the typical dimension of a typical key cap is about 14 mm×13.5 mm×1.8 mm. The air gap between a bottom surface of the key and the base plate is typically about 1.2 to 2.5 mm. In addition, use of an interconnect cable or wire is difficult and infeasible from an assembly standpoint for high volume production. Further, use of an interconnect cable or wire can interfere with other components when the key is in a vertical motion. Also, use of interconnect cables or wires can impact the operating pressure. For example, the operating pressure can increase and become inconsistent with the use of interconnected cables or wires and hence, impacts the usability of key. Also, the use of interconnect cable/wiring is not reliable to withstand multi-million operations. Use of wireless energy transfer solution is also expensive and increases power consumption. In the past, an electrical contact to a key has been attempted by creating a customized electromechanical switch. However, the addition of new parts to make the electrical connection under each key increases the overall weight, expensive, and can be complex to assemble. For example, many current keys include a dome/scissor assembly with 3-layer PET for a conductive membrane based switch and require simple snap fit assembly. Electro-mechanical based tactile switch often requires additional parts and a special tool for assembly. Further, the keys require diligent periodic maintenance or periodic cleaning of dust and can require periodic greasing to reduce the noise level of the keys as the additional mechanical parts seems to make the key vulnerable to noise if not regularly maintained.

Interactive or intelligent customizable keyboards in the past typically employ custom and sophisticated designs. They often utilize custom parts and connection mechanisms that add significant cost thereby limiting their usability. Interactive customizable keyboards can also change the fundamental feel of using a keyboard thereby limiting their acceptance. For example, often interactive customizable keyboards are bulkier, the display is at a visual depth from the surface of the key, the display has a limited viewing angle and brightness, the surface finish is not similar to conventional keyboards, the keys feel more "clicky" or do not have any tactile response, etc. In addition, the interactive customizable keyboards often demand more maintenance from end users and consume a relatively high amount of power.

Because an acceptable electrical connection is not available at the key, the typical keycap does not contain an active element like a display or sensor. One reason for this is because given the thin mechanical profile, surface topology, viewing, and lifetime requirements of a key, it can be difficult to embed active element inside a keycap without compromising use of the key. For example, the current process to design and build displays in a keycap has multiple problems. One such problem is ghosting. Ghosting can occur when the insulation gap between adjacent bottom electrodes leaves the dielectrics in that region in an in-deterministic state after few cycles of state change. As a result, the entire display needs a periodic full screen refresh. Ghosting can spoil the user experience.

One solution to mitigate ghosting is to refresh the entire display. However, refreshing the entire display (as opposed to a portion of display) increases the overall system power consumption. Another common problem is an aspect ratio mismatch where the aspect ratio of an outer dimension of a display is not same as the aspect ratio of an active display region. An aspect ratio mismatch can occur when the area required to make a connection from a bottom electrode to a top electrode is outside the active area. This causes a situation where the aspect ratio of active area is not same as the aspect ratio of the outer dimension and can introduce constrains to the aesthetics as well as the mechanical and industrial design. Also, additional space (in the X and Y plane) is required which is not always available, especially on special or small displays.

Another possible issue is that the display cannot be made with a zero or near zero millimeter (mm) bezel because the top electrode connection and edges (e.g., inactive protective edges to protect the dielectric from environment, heat seal, etc.) add a margin to the display. An active area is the actual visible area of a display and a border is required to laminate all layers of stack with a heat seal or a similar process to prevent the dielectric from being exposed to moisture. In addition, design rule constraints can introduce issues or problems. For example, an insulation gap between adjacent bottom electrodes (segments) depends on the dielectric and the material used for the base substrate and the minimum spacing in the graphic artwork (being created on bottom electrode) is limited by the insulation gap.

The electrical interface of an interactive customizable keyboard can also create problems as the connection to bottom electrodes is brought out through printed silver traces (or equivalent material). This causes the traces to extend outside the active area on the same horizontal plane of the base substrate to form a tail. If the display drive PCB is directly underneath the display, then an additional area (in the X and Y plane) to allow for a bending radius for the tail is required. Further, the process to remove dielectric material (to enable electrical connection to the top electrode) is manual and can take a significant amount of time and require a relatively large area of removal.

Key 108 can be configured to change a traditional keyboard from a passive device to an intelligent, interactive customizable device while at the same time overcoming some of the above issues. In an embodiment, key 108 can be configured to change a traditional keyboard from a passive device to an intelligent, interactive customizable device with a display, while at the same time overcoming some of the above issues. Keyboard portion 106 and key 108 can utilize the elements or components of existing keyboards with few modifications and no significant impact to usability, productivity, feel, or reliability as compared to traditional keyboards. Keyboard portion 106 and key 108 can have relatively minimal cost addition and minimal impact to assembly as compared to traditional keyboards. Further, keyboard portion 106 and key 108 can have little or no added maintenance and relatively low additional power consumption as compared to a traditional keyboard. As the same elements or components are used as a regular mechanical keyboard, there can be co-existence of traditional keys and active keys within the same system. For example, one row in keyboard portion 106 can be active while the rest of the keyboard uses traditional mechanical keys.

In addition, keyboard portion 106 can be configured to provide an interactive customizable keyboard that provides an interactive and contextual experience without compromising on the feel, function, or reliability of traditional keyboards. The basic elements of a traditional mechanical keyboard like keycap, silicone dome, scissor, base plate, scan matrix are all retained with modifications to certain elements. In an example, a key can include an embed segmented bi-stable e-paper display that can change state interactively based on user input or contextually (content or application displayed on the screen).

Keyboard portion 106 can be configured to use existing keyboard components as ingredients and use similar assembly methods. In addition, keyboard portion 106 does not impact the feel or function of traditional keyboards and can be implemented even within small Z-height keycaps, existing ergonomic layout considerations like pitch and spacing can remain virtually unaffected, no change or minimal change to operating force or travel, texture and curvature for ergonomics of keys can be maintained as per traditional keyboards, and significant height or weight compared with traditional keyboards is not added. Further, existing form factors can be retained and an interactive component such as a display can appear to be right at the surface of the typing surface as in traditional keyboards to provide an almost 180 degree viewing angle. This can also allow the keyboard to be daylight readable. In addition, keyboard portion 106 can be configured for reliable operation for multimillion cycles as in traditional keyboards and have no additional maintenance or cleaning required. Further, relatively low power is consumed (power is consumed only during state change) as state is retained even after the power is removed. This and other factors allow for a relatively minimal cost addition to implement keyboard portion 106.

In addition, an active element such as a display as outlined here can resolve the active keycap issues (and others) mentioned above. In an example, the display can be configured to print or integrate a colored mask on an outer most surface or user facing side of a display. In an example, two artworks may be prepared instead of the typical one artwork. The two artworks can include a coarse artwork for a bottom electrode or base substrate and a fine artwork for a mask or top layer. The fine artwork can be unconstrained by design rules of an underlying dielectric layer. A matte or glossy overcoat may be used to create uniform surface texture such that there is no mismatch between the surface texture of exposed areas and the mask printed area. The dielectric may be removed from the active area. In addition, a laser ablation may be used for dielectric removal. With laser ablation, the removal process can be made faster and the dimensions of the dielectric removal area can be made significantly smaller. In an example, the dielectric removal area can be made small enough to not be noticed or perceived by the naked eye of a typical user. Where a large area is required and the area is noticeable, the region can be covered with the mask. Further, a Z axis adhesive may be used and may be a conductive via or channel on the base substrate to establish an electrical connection to the segments instead of using a traditional tail.

The display can be configured to reduce or eliminate visible ghosting and reduce power consumption as a global refresh is not required. With coarse artwork for the bottom electrode and fine artwork on top of the display, the area which is undergoing a ghosting effect can be hidden. The ghosting effect is present, but it is not visible to the user because the mask can cover or hide the area where the ghosting would occur. In addition, the display can allow for finer graphics because visible artwork is not dependent on design rules of the dielectric layer. The display can also allow for a uniform aspect ratio of an active area and an outer dimension if the display can be laminated or allow for a zero mm bezel if the display is not laminated. Also, the number of drive lines can be reduced by one because a background segment is not required with a mask. Reducing the drive lines by one can be an advantage in tight space constraints. The display can further be configured to avoid the requirement of a display tail and the area required for its bending radius. This can be an advantage when the display is used in very small applications such as wearable or a keycap of a keyboard.

In an example, a user facing side of the display can be printed with a mask layer. The graphic on the mask can be very fine and independent of the design rules applicable on a bottom electrode or base substrate. The mask serves as the background and has the same color as the background segment (if it was present). The mask may have matte or glossy finish to match the look and feel of a traditional keycap. The area that is left exposed by the mask can be coated with a transparent overcoat. The thickness of overcoat can have the same as the thickness of mask ink. The finish of a transparent overcoat (glossy or matte) is kept same as the finish of ink used for printing the mask.

The display can include a coarse graphic printed on a bottom electrode or base substrate. If the background color is black, then a character printed on the mask is made visible by driving the bottom electrode to a white state. Similarly, the character printed with a mask can be driven to a hidden state by driving the bottom electrode to a black state. The display created by the bottom electrode can be used like the concept of backlight. The thickness and finish match of transparent overcoat applied on exposed area is same as the thickness and finish of the ink used for mask. The color used for mask can be the same as the effective color of a background segment as seen through the overcoat. This ensures that a hidden state can be effectively achieved.

For connecting the top electrode, the dielectric can be removed from active area itself. The dead region created by dielectric removal can be hidden by the mask. Since the dielectric removal can be performed by laser ablation, the size of the dead region is limited to a small dimension to minimize the loss of a display region within the active area. The insulation gap between adjacent bottom electrodes can also be hidden by the mask. As a result, the ghosting effect is never visible to a user. In an example, the base substrate (e.g., PET or FR4 or polyimide) can include conductive vias. The electrical connection to bottom electrode can be established to a PCB using a Z axis adhesive.

In one or more embodiments, the display can be included in a device that may include a battery and various components of an electronic system. The components may include a central processing unit (CPU), a memory, etc. Any processors (inclusive of digital signal processors, microprocessors, supporting chipsets, etc.), memory elements, etc. can be suitably coupled to a motherboard based on particular configuration needs, processing demands, computer designs, etc. Other components such as external storage, controllers for video display, sound, and peripheral devices may be attached to the motherboard as plug-in cards, via cables, or integrated into the motherboard itself.

Turning to FIG. 2A, FIG. 2A is a cross section side view of key 108, in accordance with one embodiment of the present disclosure. Key 108 can include keycap 110, scissors 112, and a dome 114. In an example, a coating can be applied on a dome already present in a keyboard structure to make the dome conductive. The coating can be etched to create multiple electrical paths on the body of dome 114. The coating treatment ensures conductivity over multi-million operations without impacting operating pressure (force and strike response of dome).

Key 108 does not require a new electro-mechanical switch design and reuses existing mature ingredients of a keyboard which are proven over several decades and are broadly available. In addition, key 108 does not require any new additional component for electrical interconnection. Hence there is no interference with a mechanical switch. Further, the system does not add new assembly steps for the interconnection of the elements. The connection is established using existing processes of a keyboard assemble and does not impact the operating pressure of keyboard. Also, key 108 does not require any additional (or no more than a typical mechanical keyboard assembly) periodical maintenance, disassembly, cleaning, reassembly and verification or require nominal cleaning. The system can provide reliable electrical and mechanical functionality over multi-million operations with no additional maintenance. Key 108 system is relatively inexpensive, relatively light, and there is no deviation or relatively minor deviation from to the shape and size of a traditional key.

During use, dome 114 can include silicone, metallic, or any other equivalent element that can absorb the operating pressure when key 108 is pressed and then strike back key 108 to its original position when the operating pressure is removed. Such a retractive element has to maintain consistent contact with a bottom side of key 108 at a top end of dome 114 and a bottom structural foundation of a keyboard module to facilitate smooth tactile motion. This structural requirement can be used to establish an electrical connection between a keycap and the rest of the system. The surface of dome 114 can be modified to include multiple electrical paths and is not limited to the illustrations, embodiments, or designs discussed herein.

Figure 2B:
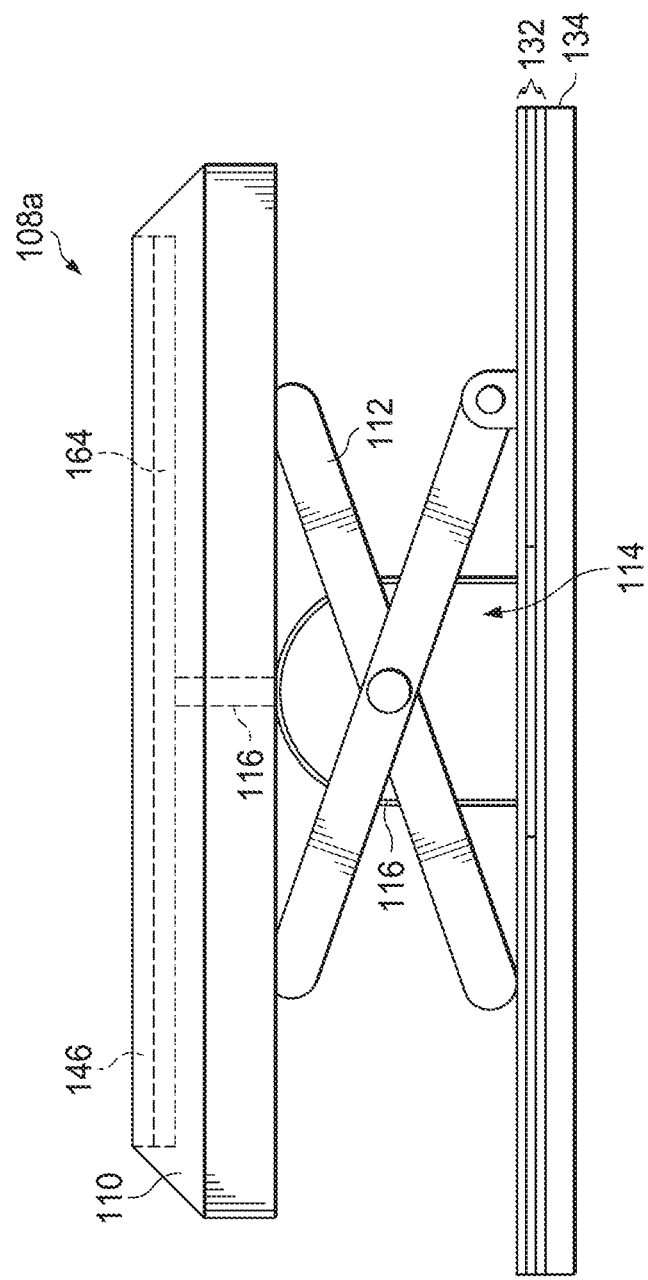
FIG. 2B is a simplified schematic diagram illustrating a plan view of an embodiment of a portion of a keyboard, in accordance with one embodiment of the present disclosure.

Turning to FIG. 2B, FIG. 2B is a cross section side view of key 108a, in accordance with one embodiment of the present disclosure. Key 108a can include keycap 110, scissors 112, and a dome 114. Keycap 110 can include a resin layer 146 and an active element 164. Dome 114 can be coupled to a scan matrix layer 132 on a base substrate 134.

Active element 164 can be coupled to or in communication with scan matrix layer 132 through a conductive area 116 that extends over dome 114. Conductive area 116 can be a coating applied on dome 114 to make dome 114 conductive. The coating can be etched to create multiple electrical paths on the body of dome 114 can ensure conductivity over multi-million operations without impacting operating pressure (force and strike response of dome).

Figure 3:
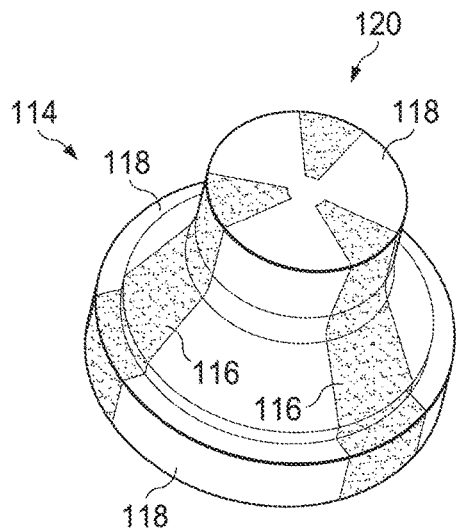
FIG. 3 is a simplified schematic diagram illustrating an orthographic view of an embodiment of a portion of a keyboard, in accordance with one embodiment of the present disclosure.

Turning to FIG. 3, FIG. 3 illustrates one example of dome 114. Dome 114 can include one or more conductive areas 116, one or more non-conductive areas 118, and a top portion 120. In an example, top portion 120 would be in contact with keycap 110. Each conductive area 116 can be an electrical trace. Non-conductive area 118 can isolate conductive areas 116 from each other.

Figure 4:
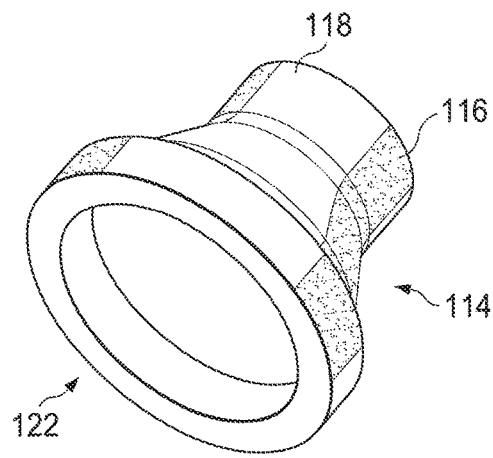
FIG. 4 is a simplified schematic diagram illustrating an orthographic view of an embodiment of a portion of a keyboard, in accordance with one embodiment of the present disclosure.

Turning to FIG. 4, FIG. 4 illustrates one example of dome 114. The width of conductive area 116 and non-conductive area 118 can be equal or may be different. In an example, each conductive area 116 on dome 114 can be electrically connected to the rest of the system using conductive adhesive applied at bottom side 122 of dome 114. Different embodiments can increase or decrease the number of conductive areas 116 and can change the width of each conductive area 116 and non-conductive area 118.

Figure 5A:
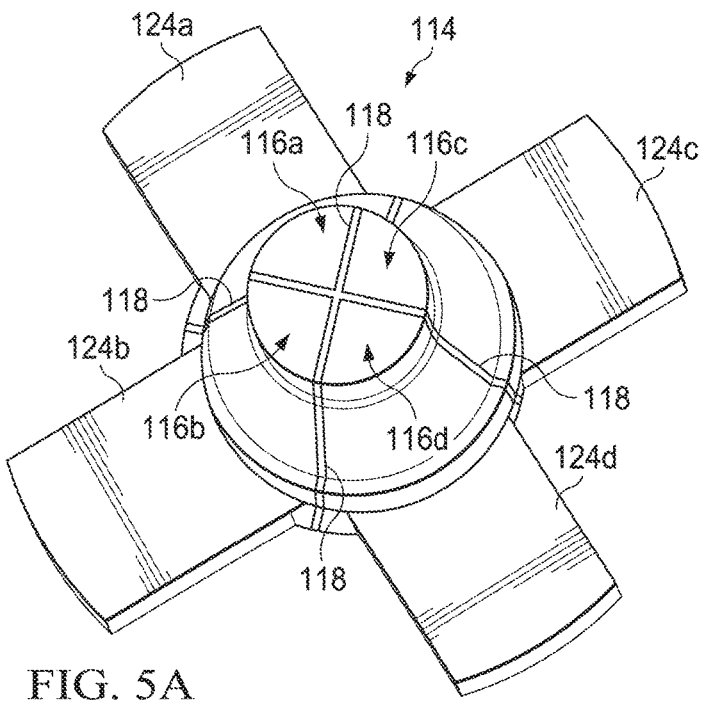
FIG. 5A is a simplified schematic diagram illustrating an orthographic view of an embodiment of a portion of a keyboard, in accordance with one embodiment of the present disclosure.

Turning to FIG. 5A, FIG. 5A illustrates one example of dome 114. As illustrated in FIG. 5A, dome 114 can include four conductive areas 116a-116d and nonconductive area 118. Deposition to create conductive areas 116a-116d can be performed on the body of dome 114 and the substrate on which dome 114 is bonded. For example, conductive areas 116a-116d on dome can be electrically coupled to traces 124a-124d respectively. In some examples, dome 114 can be electrically coupled to the rest of the system using conductive adhesive applied on the base substrate of dome 114 which can also be coated and etched. Etching can be performed on dome 114 and the base substrate. In this example, conductive areas 116a-116d are much larger as compared to non-conductive area 118.

Figure 5B:
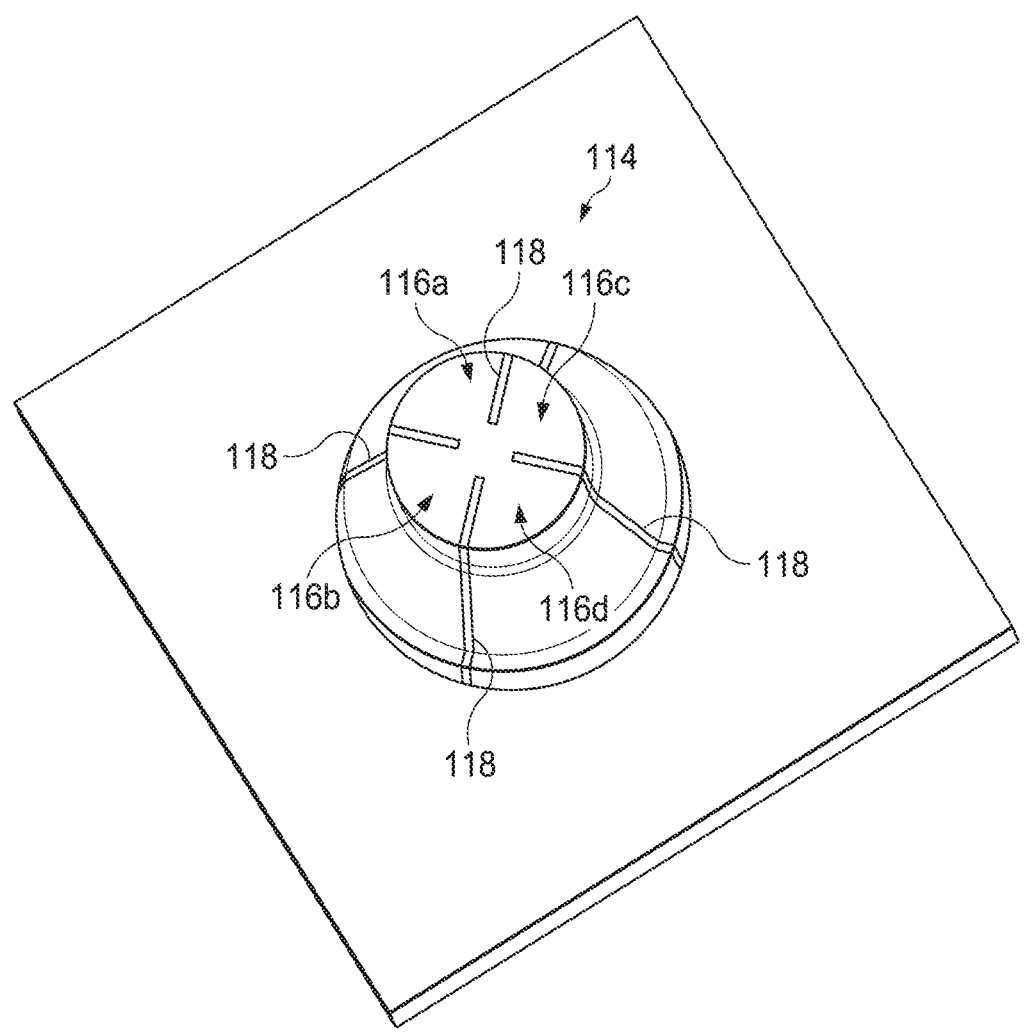
FIG. 5B is a simplified schematic diagram illustrating an orthographic view of an embodiment of a portion of a keyboard, in accordance with one embodiment of the present disclosure.

Turning to FIG. 5B, FIG. 5B illustrates one example of dome 114. As illustrated in FIG. 5B, dome 114 can include four conductive areas 116a-116d and nonconductive area 118. Nonconductive area 118 can be extended to create electrical isolation for conductive areas 116a-116d. In an example, dome 114 and a transmitter sheet are not two separate parts but are a single part design where during manufacture, only the domes are first bonded directly on a transmitter sheet (without any traces 124a-124d illustrated in FIG. 5A). The assembled sheet can then be coated with a conductive coating. The coating connects directly with conductive pads printed on a transmitter sheet. After coating, electrical isolation can be created on dome 114 with a laser etch process. Laser etching can also be used to create electrical isolation on the bottom of the transmitter sheet. The pattern of laser etching on the bottom of the transmitter sheet can be similar to the pattern of traces 124a-124d illustrated in FIG. 5A.

Figure 6A:
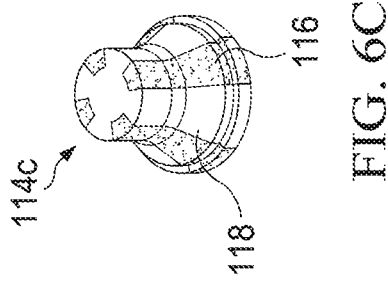
FIG. 6A is a simplified schematic diagram illustrating an orthographic view of an embodiment of a portion of a keyboard, in accordance with one embodiment of the present disclosure.
Figure 6D:
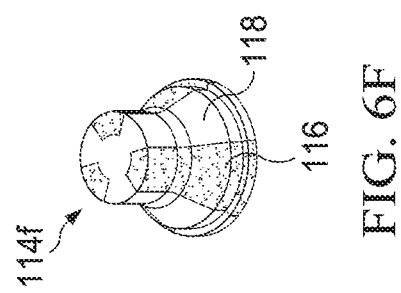
FIG. 6D is a simplified schematic diagram illustrating an orthographic view of an embodiment of a portion of a keyboard, in accordance with one embodiment of the present disclosure.
Figure 6B:
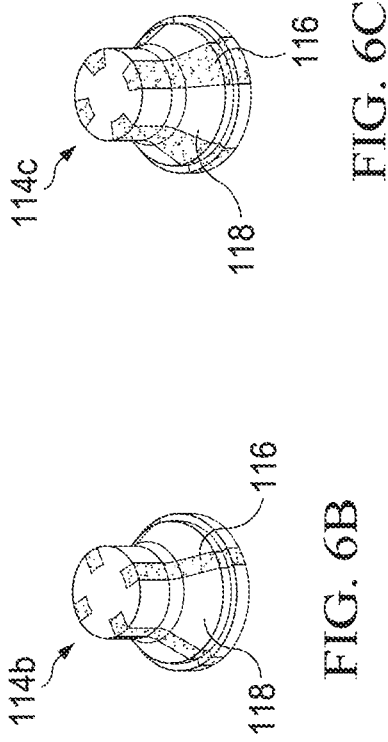
FIG. 6B is a simplified schematic diagram illustrating an orthographic view of an embodiment of a portion of a keyboard, in accordance with one embodiment of the present disclosure.
Figure 6E:
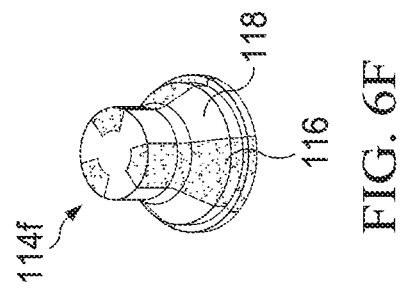
FIG. 6E is a simplified schematic diagram illustrating an orthographic view of an embodiment of a portion of a keyboard, in accordance with one embodiment of the present disclosure.
Figure 6C:
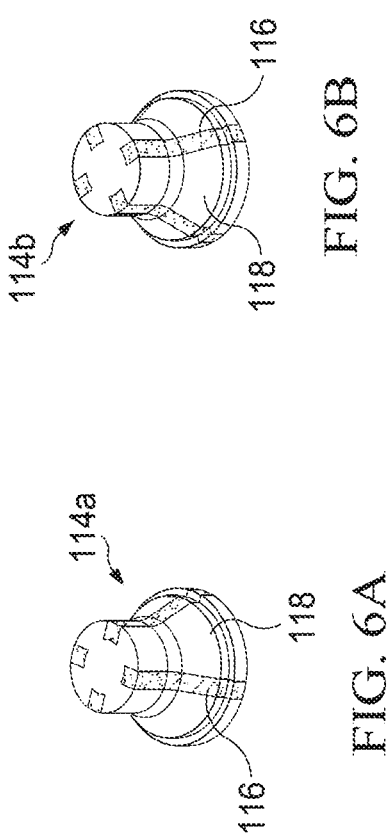
FIG. 6C is a simplified schematic diagram illustrating an orthographic view of an embodiment of a portion of a keyboard, in accordance with one embodiment of the present disclosure.
Figure 6F:
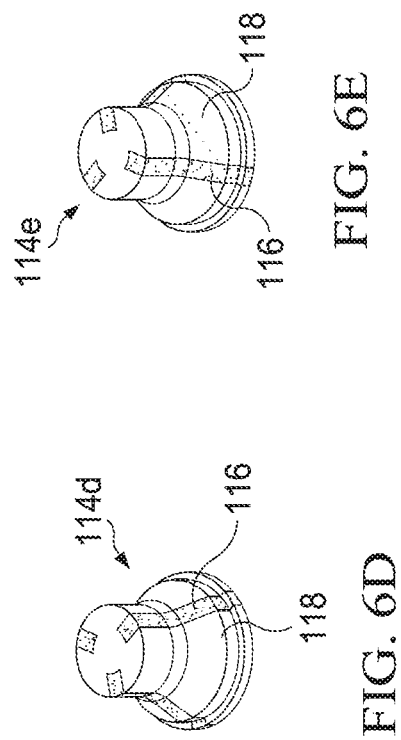
FIG. 6F is a simplified schematic diagram illustrating an orthographic view of an embodiment of a portion of a keyboard, in accordance with one embodiment of the present disclosure.

Turning to FIGS. 6A-6F, FIGS. 6A-6F illustrates examples of different embodiments of a dome. As illustrated in FIGS. 6A-6F, each dome 114a-114f may have a different number of conductive areas 116 and/or a different width of each conductive area 116. For example, as illustrated in FIG. 6A, dome 114a has four relatively large conductive areas 116, while, as illustrated in FIG. 6E dome 114e has three relatively small conductive areas 116. The number and thickness of conductive areas is only limited by design constraints and user preferences.

Figure 7:
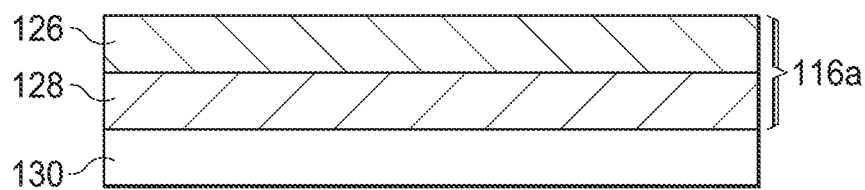
FIG. 7 is a simplified schematic diagram illustrating a side block diagram view of an embodiment of a portion of a keyboard, in accordance with one embodiment of the present disclosure.

Turning to FIG. 7, FIG. 7 illustrates one example of a portion of a conductive dome. As illustrated in FIG. 7, a portion of a conductive dome can include a first layer 126, a second layer 128, and a third layer 130. First layer 126 and second layer 128 can be combined into conductive area 116. First layer 126 can include a thin coating of a metallic material that is electrically conductive. First layer 126 can also have strong adhesion properties with second layer 128. Second layer 128 can include a thin coating of metallic material that may be the same as first layer 126 or may be a different material than first layer 126. Second layer can have strong adhesion properties to third layer 130. Third layer 130 includes the outer surface of dome 114 and may include silicon or some other similar material. In an example, first layer 126 may be a material that will not bond or is difficult to bond with third layer 130. Second layer 128 can be configured to help bond first layer 126 to third layer 130.

Figure 8:
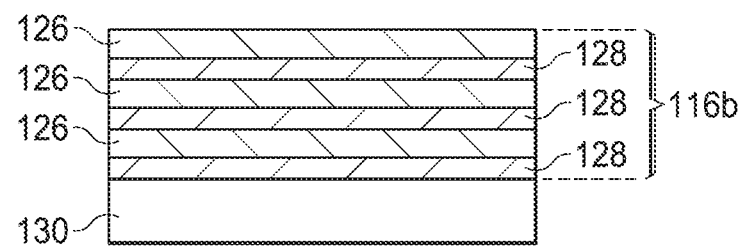
FIG. 8 is a simplified schematic diagram illustrating a side block diagram view of an embodiment of a portion of a keyboard, in accordance with one embodiment of the present disclosure.

Turning to FIG. 8, FIG. 8 illustrates one example of a portion of a conductive dome. As illustrated in FIG. 8, a portion of the conductive dome can include a plurality of first layers 126, a plurality of second layers 128, and third layer 130. The plurality of first layers 126 and second layers 128 can be combined into conductive area 116b. Each first layer 126 may be about 0.1 microns thick and each second layer 128 may be about 0.025 microns thick.

In an example, the surface of dome 114 may be coated with physical vapor deposition or any other similar coating technique. In another example, only one material such as Nickel Titanium is used and only one layer is coated. The overall thickness of the coating can vary from sub-micron to few microns depending on the target material used for deposition and the material composition of silicone.

Figure 9:
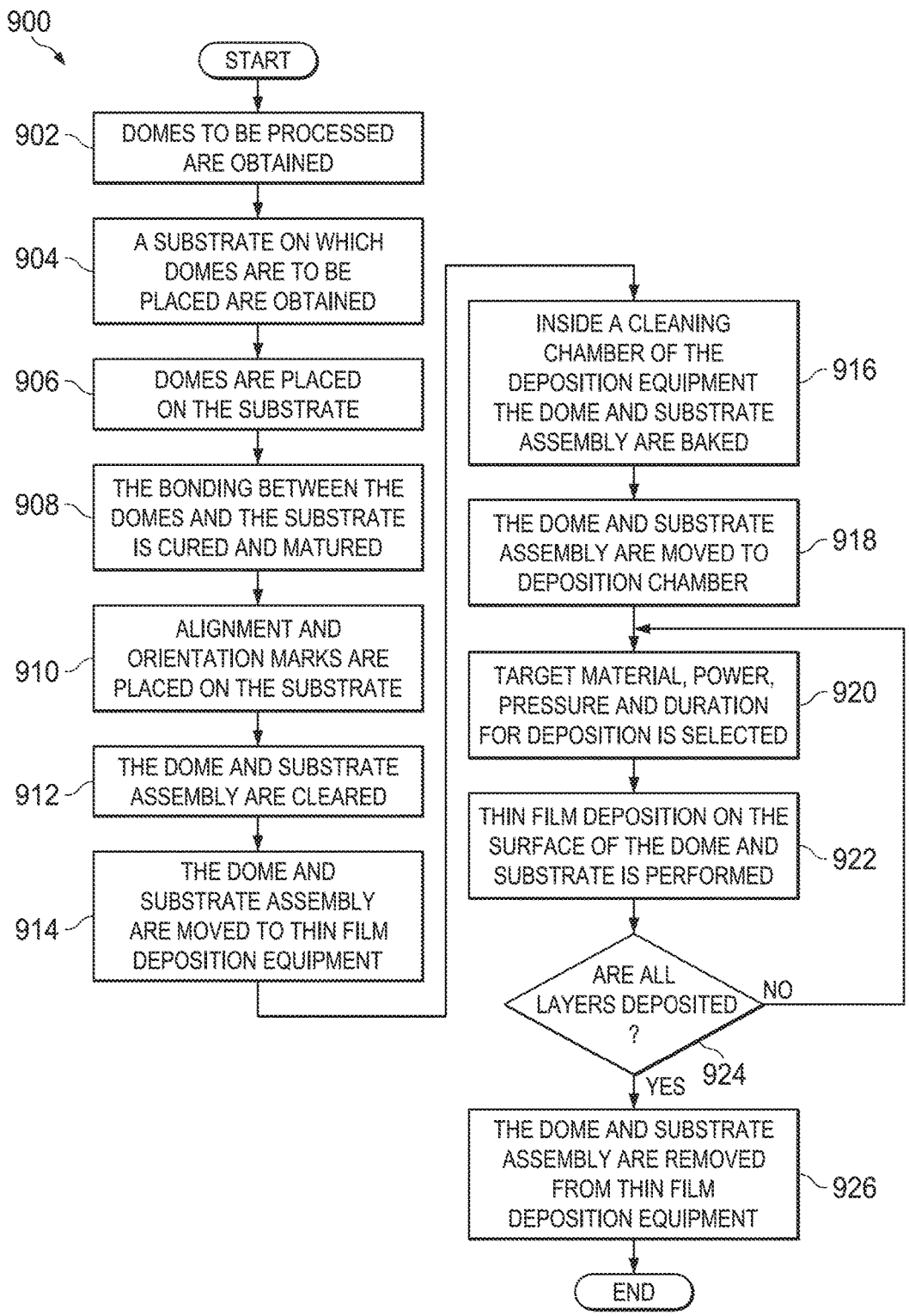
FIG. 9 is a simplified a simplified flow diagram illustrating potential operations associated with one embodiment of the present disclosure.

Turning to FIG. 9, FIG. 9 is an example flowchart illustrating possible operations of a flow 900 that may be associated with the present disclosure. At 902, domes to be processed are obtained or identified. At 904, a substrate on which the domes are to (or should) be placed are obtained or identified. At 906, the domes are placed on the substrate. In an example, the domes are placed on the substrate using adhesive. At 908, the bonding between the domes and the substrate is cured and matured. At 910, alignment and orientation marks are placed on the substrate. At 912, the dome and substrate assembly are cleared or cleaned. At 914, the dome and substrate assembly are moved to thin film deposition equipment. At 916, inside a cleaning chamber of the deposition equipment, the dome and substrate assembly are baked. At 918, the dome and substrate assembly are moved to a deposition chamber. At 920, target material, power, pressure, and duration for deposition are selected. At 922, thin film deposition on the surface of the dome and substrate is performed. At 924, the system determines if all the layers have been deposited. If all the layers have not been deposited, then the system returns to 920 and target material, power, pressure, and duration for deposition are again selected. If all of the layers have been deposited, then the dome and substrate assembly are removed from the thin film deposition equipment, as in 926.

Figure 10:
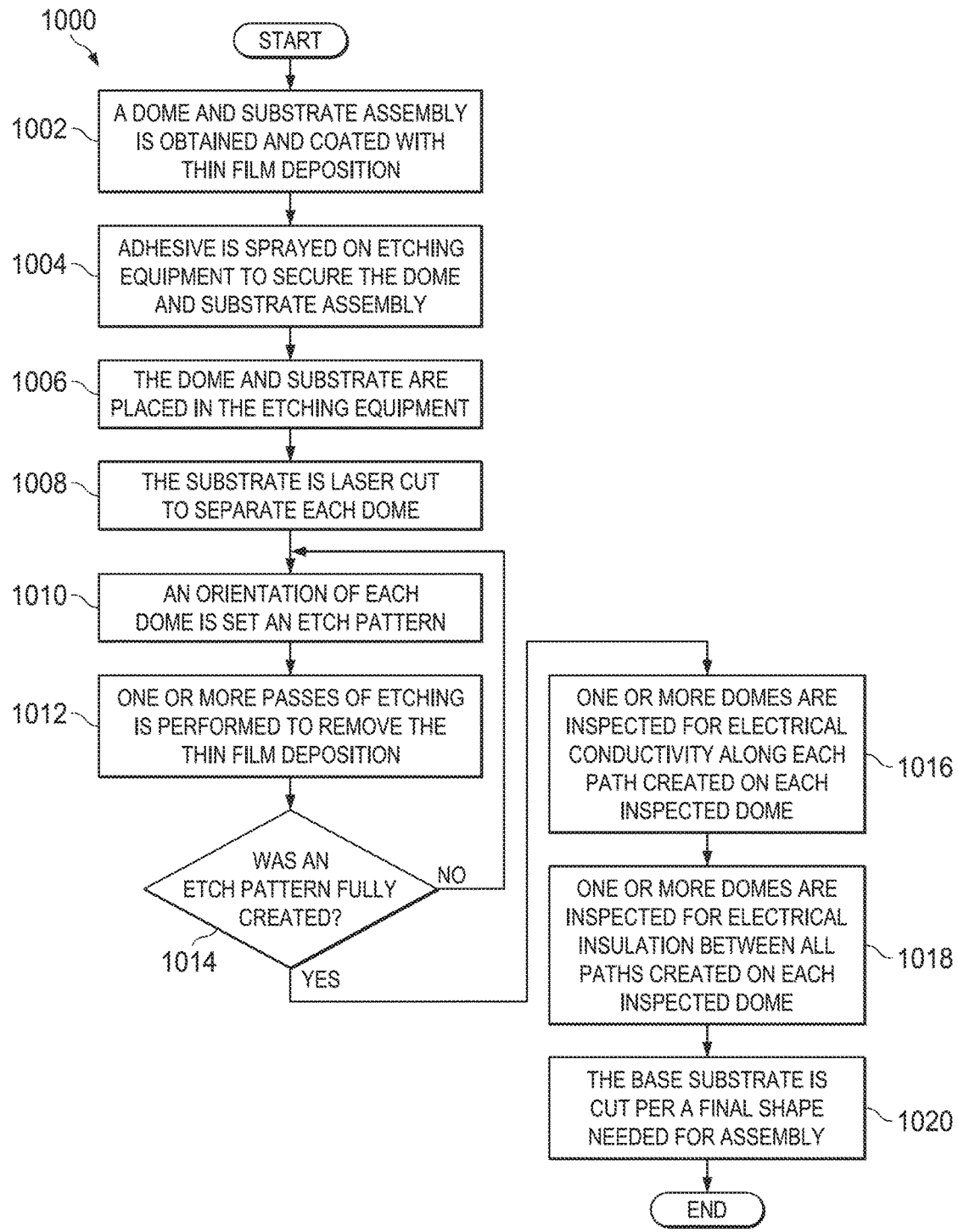
FIG. 10 is a simplified a simplified flow diagram illustrating potential operations associated with one embodiment of the present disclosure.

Turning to FIG. 10, FIG. 10 is an example flowchart illustrating possible operations of a flow 1000 that may be associated with the present disclosure. At 1002, a dome and substrate assembly are obtained (or located) and coated with thin film deposition. At 1004, adhesive is sprayed on etching equipment (e.g., laser etch equipment) to secure the dome and substrate assembly to the etching equipment. At 1006, the dome and substrate assembly are placed in the etching equipment. In an example, the dome and substrate assembly are aligned and orientated using the marks made on the substrate (as in flow 900, illustrated in FIG. 9). At 1008, the substrate is laser cut to separate each dome. In an example, a portion of the substrate associated with each dome is also cut. In another example, in a single part design, the substrate is not cut and is only etched to create electrical isolation on the substrate. At 1010, an orientation of each dome is set as per an etch pattern. In an example, the etch pattern may be a laser etch pattern. At 1012, one or more passes of etching is performed to remove the thin film deposition. At 1014, the system determines if an etch pattern was fully created. If the etch pattern was not fully created, then the system returns to 1010 and an orientation of each dome is set as per an etch pattern. If the laser etch pattern was fully created, then one or more domes are inspected for electrical conductivity along each patch created on the dome, as in 1016. At 1018, one or more domes are inspected for electrical insulation between all the paths created on the dome. At 1020, the base substrate is cut per a final shape needed for assembly.

Figure 11:
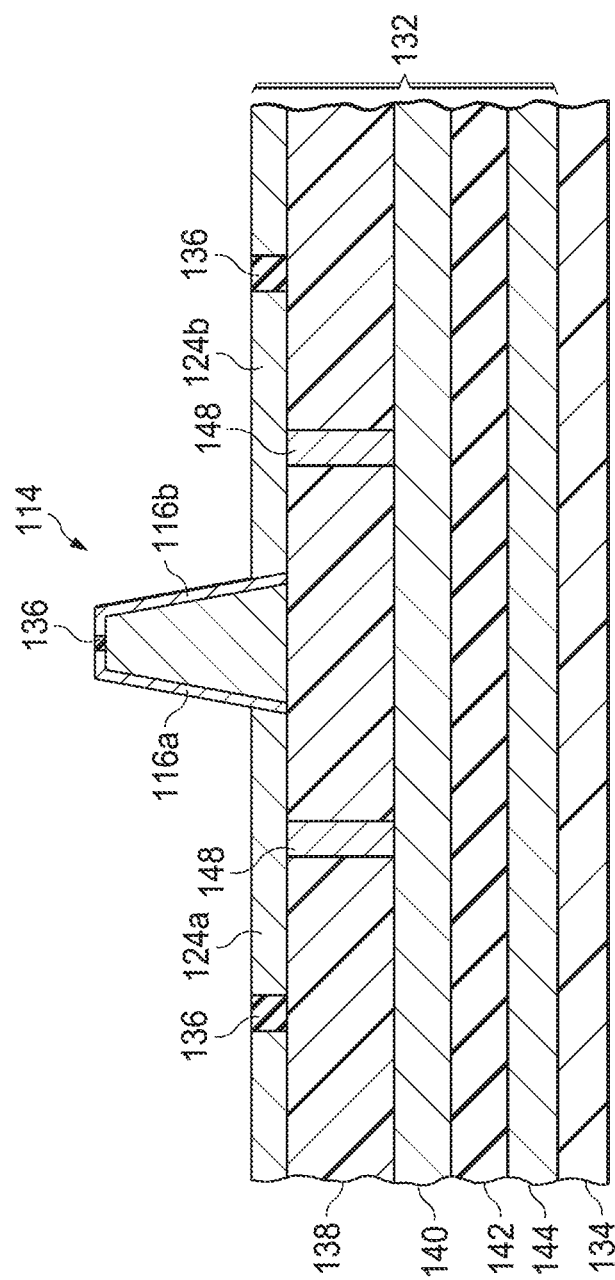
FIG. 11 is a simplified schematic diagram illustrating a side block diagram view of an embodiment of a portion of a keyboard, in accordance with one embodiment of the present disclosure.

Turning to FIG. 11, FIG. 11 is a cross section side view of a portion of a keyboard (e.g., keyboard 106), in accordance with one embodiment of the present disclosure. In an example, a portion of a keyboard (e.g., keyboard 106) can include dome 114, conductive areas 116a and 116b, a scan matrix layer 132, and a base substrate 134. Scan matrix layer 132 can include isolation region 136, support layer 138, tracings 140, insulation coating 142, and scan matrix 144. Isolation regions 136 can isolate signals or communications on one conductive area (e.g., conductive area 116a) from signals or communications on another conductive area (e.g., conductive area 116b) and from the rest of the system. Vias 148 can provide a communication path between conductive areas 116a and 116b and tracings 140. Tracings 140 can allow signals and communications to be be communicated to a processor such as one in a transmitter board or host controller board. Support layer 138 can be a substrate and can include a polyester such as polyethylene terephthalate (PET). Scan matrix 144 can include scan matrix traces.

Figure 12:
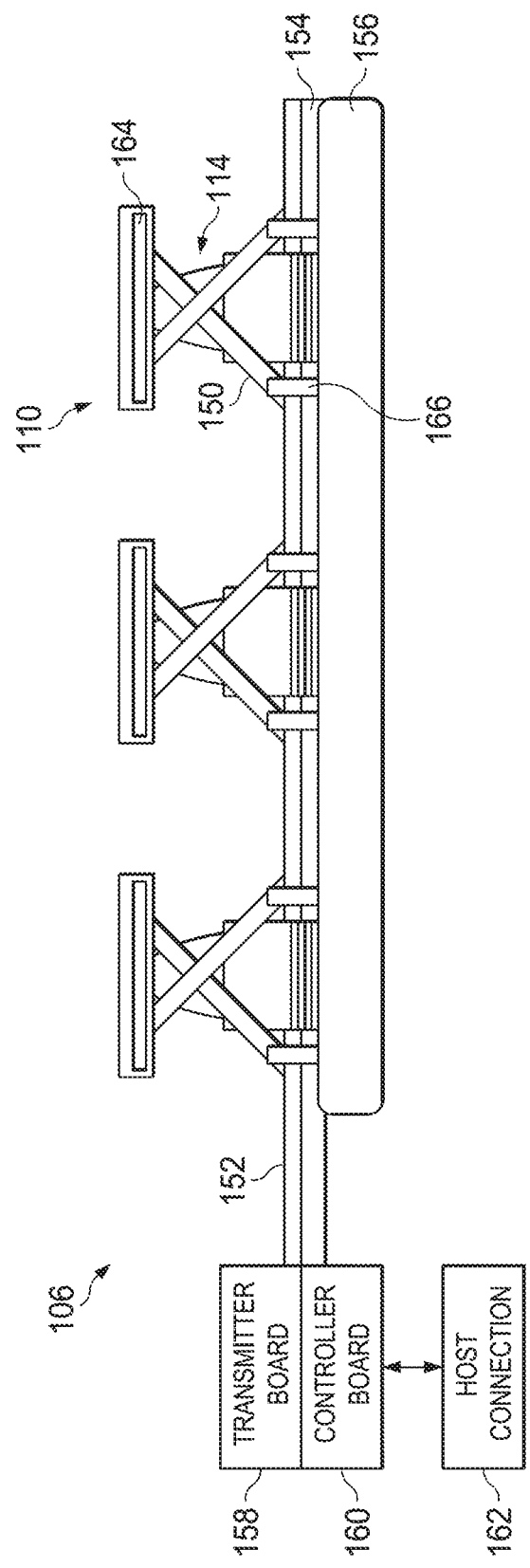
FIG. 12 is a simplified schematic diagram illustrating a side block diagram view of an embodiment of a portion of a keyboard, in accordance with one embodiment of the present disclosure.

Turning to FIG. 12, FIG. 12 illustrates one example of keyboard portion 106. Keyboard portion 106 can include keycap 110, dome 114, scissors 150, a communication path 152, a transmitter sheet 154, a base plate 156, a transmitter board 158, a controller board 160, and a host connection 162. Keycap 110 can include an active element 164 (e.g., a display, bi-stable display, e-ink display, etc.). Scissors 150 can be coupled to base plate 156 using locking mechanism 166. In an example, transmitter sheet 168 can be similar to tracings 140 and can allow signals and communications to be be communicated between keycap 110 and a transmitter board 158 or a controller board 160. Transmitter board 158 can be configured to control active element 164 in keycap 110. Controller board 160 can be configured to control or send communications to transmitter board 158. In an example, controller board 160 can include logic or instructions that can be communicated to transmitter board 158 and transmitter board can function as a driver to cause active element 164 to perform a function or action. Host interface 162 can be configured to communicate with various electronics (e.g., main motherboard) of second housing 104. In an example, tracing 140 can be done on a transmitter sheet to connect each conductive path on dome 114 to the output of transmitter board 158. There may be space constraints to route the traces on the transmitter sheet because the transmitter sheet can include a plurality of holes. The plurality of holes can allow a locking mechanism to protrude out from an underlying baseplate. The tracing in limited areas can be optimized by combing drive lines that always carry the same differential voltage signals in different electrodes. The optimization can be done even when the electrodes belong to different keys.

Figure 13:
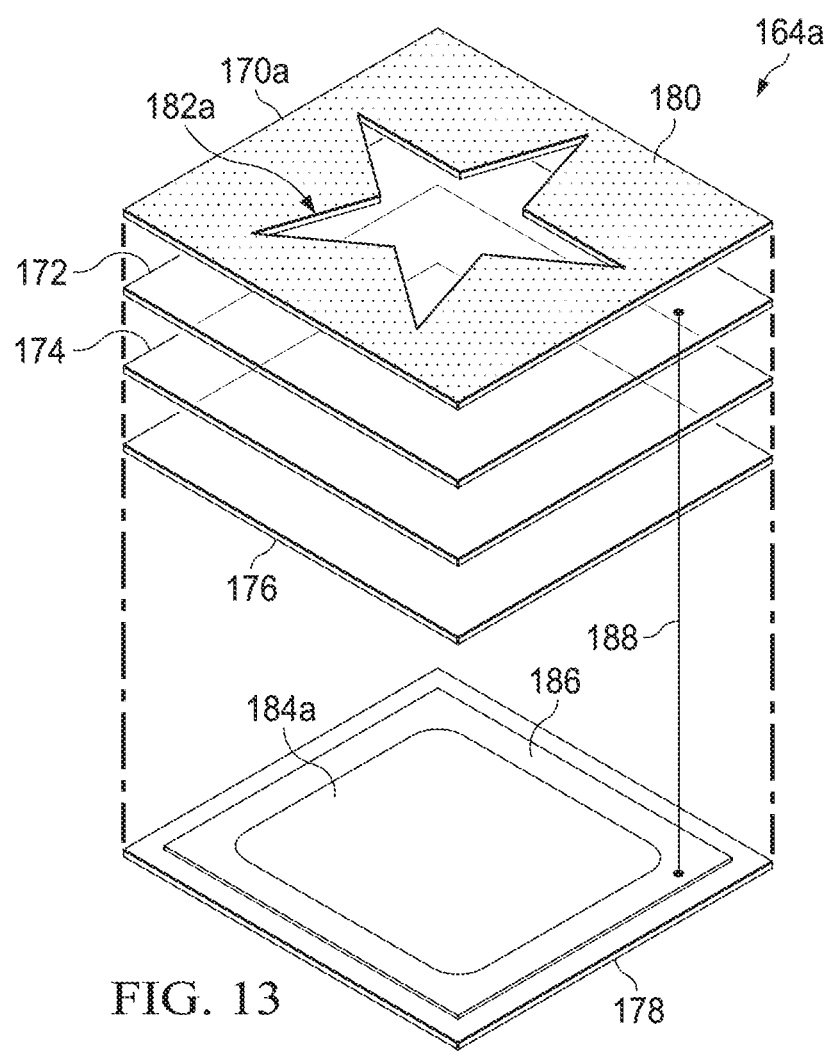
FIG. 13 is a simplified schematic diagram illustrating an exploded block diagram view of an embodiment of a portion of a key, in accordance with one embodiment of the present disclosure.

Turning to FIG. 13, FIG. 13 is a simplified plan view illustrating an embodiment of an active element 164a in accordance with one embodiment of the present disclosure. Active element 164a can include a transparent substrate 170a, a top electrode 172, a dielectric 174, a conductive adhesive 176, and a base substrate 178. In an example, a conductive adhesive may be located on a top side and on a bottom side of top electrode 172. Transparent substrate 170a can include a mask 180 and an exposed area 182a. While a star profile is shown as exposed area 182a, the profile can be almost any shape, number, letter, symbol, etc. Base substrate 178 can include a bottom electrode 184a and a top electrode connection area 186. Top electrode connection area 186 can be coupled to top electrode 172 using electrical path 188. In an example, there can be a one-to-one (1:1) or one-to-n (1:n) mapping between bottom electrode 184a and exposed area 182a. For example, if a symbol "!" and a number "1" are always shown or hidden at the same time, then they may both be independent (not connected) fine artwork on mask 180, but they can be controlled by one (connected) coarse artwork on bottom electrode 184a. The term "fine artwork" may be used to describe a feature or element similar to exposed area 182a and the term "course artwork" may be used to describe a feature or element similar to bottom electrode Active element 164a may be a bi-stable display. The term bi-stable refers to the ability of a display to retain content on the display even after the source of power for the display is removed. Active element 164a may be used with any suitable electronic device having a display such as a computer, mobile device, a tablet device (e.g., I-Pad™), Phablet™, a personal digital assistant (PDA), a smartphone, an audio system, a movie player of any type, etc. In an example, a thickness of top electrode 172, dielectric 174, mask 180, and bottom electrode 184a is less than about three (3) millimeters.

Top electrode 172 may be a top electrode and can be facing a user side. Top electrode 172 can include transparent conductive material like Indium Tin Oxide (ITO). The color of dielectric 174, as seen from the user facing side, can change when a differential voltage is applied across the electrodes. There are different types of bi-stable display, such as electrophoretic displays (eInk), electrochromic displays, and photonic displays. The displays differ based on the material used for the dielectric layer and all can be included in active element 164a.

As illustrated in FIG. 13, image 182a on mask 180 does not extend to top electrode connection area 186 so electrical path 188 and any ghosting effects are not visible. Base substrate 178 can include PET film, polyimide film, FR4, etc. Connective path 188 can be created by removing dielectric material and can be configured to enable a connection to top electrode 172 from base substrate 178. Electrical path 188 can be configured to allow for communication between top electrode 172 and base substrate 178.

Figure 14A:
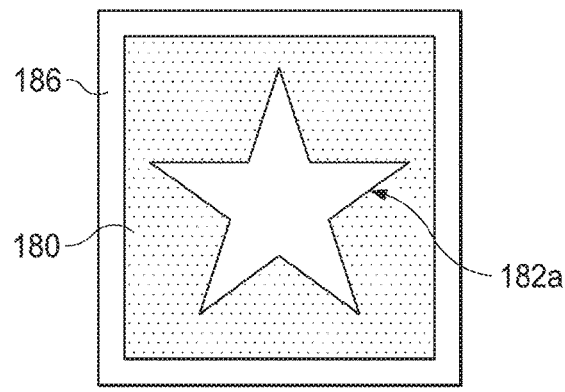
FIG. 14A is a simplified schematic diagram illustrating a block diagram view of an embodiment of a portion of a key, in accordance with one embodiment of the present disclosure.

Turning to FIG. 14A, FIG. 14A illustrates a block diagram view of an embodiment of a portion of a key (e.g., key 108) that includes a display (e.g., active element 164*a*), in accordance with one embodiment of the present disclosure. FIG. 14A illustrates an example of a display with lamination 186. When a user views the display, lamentation 186, mask 180, and exposed area 182*a* may be visible to the user. It is worth noting that electrical path 188*a* and any ghosting effects are not visible because electrical path 118*a* and any ghosting effects are hidden by mask 180.

Figure 14B:
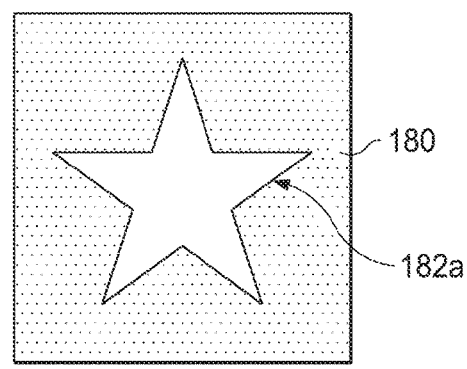
FIG. 14B is a simplified schematic diagram illustrating a block diagram view of an embodiment of a portion of a key, in accordance with one embodiment of the present disclosure.

Turning to FIG. 14B, FIG. 14B illustrates a block diagram view of an embodiment of a portion of a key (e.g., key 108) that includes a display (e.g., active element 164*a*), in accordance with one embodiment of the present disclosure. When a user views the display, mask 180 and exposed area 182*a* may be visible to the user. It is worth noting that even without lamination 186 illustrated in FIG. 14A, electrical path 188*a* and any ghosting effects are not visible because electrical path 118*a* and any ghosting effects are hidden by mask 180.

Figure 15A:
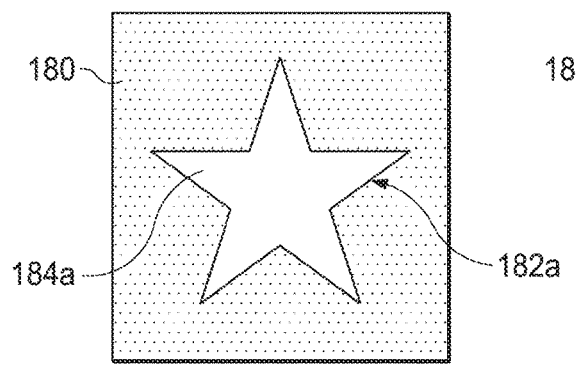
FIG. 15A is a simplified schematic diagram illustrating a block diagram view of an embodiment of a portion of a key, in accordance with one embodiment of the present disclosure.

Turning to FIG. 15A, FIG. 15A illustrates a block diagram view of an embodiment of a portion of a key, in accordance with one embodiment of the present disclosure. FIG. 15A illustrates an example of when dielectric layer is not the same or not close to the same color as mask 180. In FIG. 15A, exposed area 182*a* is visible to a user.

Figure 15B:
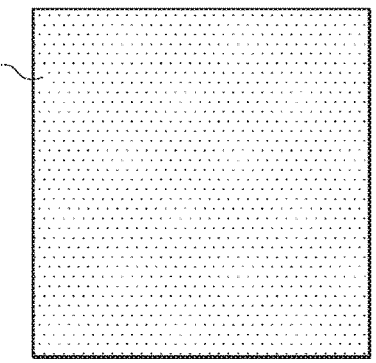
FIG. 15B is a simplified schematic diagram illustrating a block diagram view of an embodiment of a portion of a key, in accordance with one embodiment of the present disclosure.

Turning to FIG. 15B, FIG. 15B illustrates a block diagram view of an embodiment of a portion of a key, in accordance with one embodiment of the present disclosure. FIG. 15B illustrates an example of when dielectric layer is the same or close to the same color as mask 180. In FIG. 15B, exposed area 182*a* is not visible to a user.

In an example, dielectric 174 is sandwiched between top electrode 172 (a first conductor) and bottom electrode 184*a* (a second conductor). When a differential voltage is crated between top electrode 172 and bottom electrode 184*a*, the differential voltage can be used to change the state of the dielectric and cause the dielectric to produce a different color. In one example, a first differential voltage can cause dielectric 174 to appear white such that exposed area 182*a* appears white or a contrasting color to the color of mask 180 (e.g., as illustrated in FIG. 15A). When a second differential voltage is applied across top electrode 172 and bottom electrode 184*a*, the color of dielectric 174 changes to appear black or to match mask 180 and exposed area 182*a* may not be visible to the user and the user would not see any visible indication or very little indication or trace of exposed area 182*a* (e.g., as illustrated in FIG. 15B). Note that the color of dielectric mater 174 may include colors other than black and a solid color may be used or two or more different colors may be used.

Figure 16:
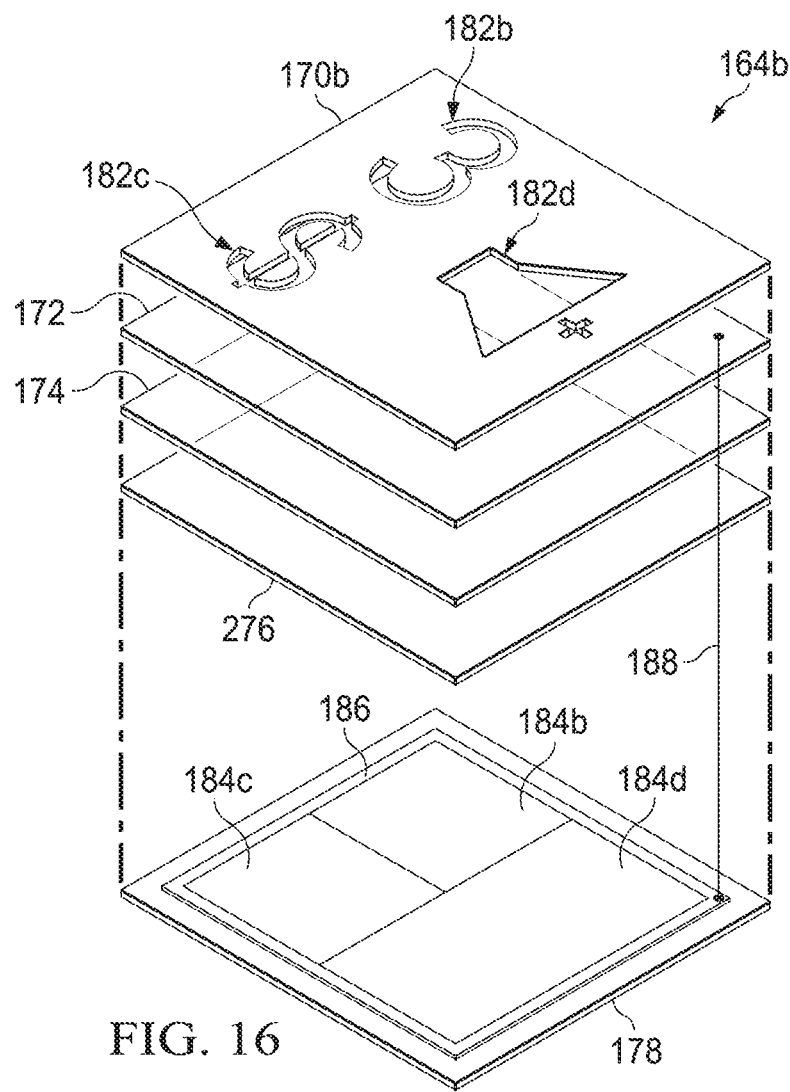
FIG. 16 is a simplified schematic diagram illustrating an exploded block diagram view of an embodiment of a portion of a key, in accordance with one embodiment of the present disclosure.

Turning to FIG. 16, FIG. 16 is a simplified plan view illustrating an embodiment of active element 164*b* in accordance with one embodiment of the present disclosure. Active element 164*b* can include a transparent substrate 170*b*, top electrode 172, dielectric 174, conductive adhesive 176, and base substrate 178. Base substrate 178 can include bottom electrodes 184*b*-184*d* and top electrode connection area 186. Top electrode connection area 186 can be coupled to top electrode 172 using electrical path 188.

Figure 17A:
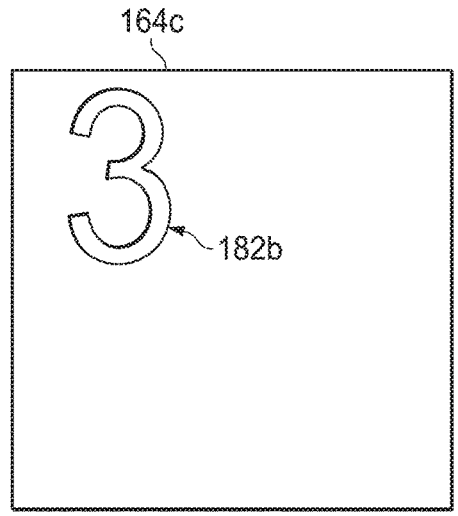
FIG. 17A is a simplified schematic diagram illustrating a block diagram view of an embodiment of a portion of a key, in accordance with one embodiment of the present disclosure.

Transparent substrate 170*b* can include a mask 180 and exposed areas 182*b*, 182*c*, and 182*d*. While a number three ("3") profile is shown as exposed area 182*b*, the profile can be almost any shape, number, letter, symbol, etc. While a dollar sign ("$") profile is shown as exposed area 182*c*, the profile can be almost any shape, number, letter, symbol, etc. While a speaker or volume profile is shown as exposed area 182*d*, the profile can be almost any shape, number, letter, symbol, etc. In an example, exposed area 182*b* can correspond with bottom electrode 184*b*, exposed area 182*c* can correspond with bottom electrode 184*c*, and exposed area 182*d* can correspond with bottom electrode 184*d*. If an exposed area on mask is small, then a coarse shape on bottom electrode can also be small. For example, there may be large inactive areas on bottom substrate that have no actual electrode. This can help in saving cost by using less material and in reducing the noise/EMI/EMC pickup by reducing the areas that need to be conductive. In an example, a thickness of top electrode 172, dielectric 174, mask 180, and bottom electrodes 184*b*-184*d* is less than about three (3) millimeters Turning to FIG. 17A, FIG. 17A is a simplified plan view illustrating an embodiment of active element 164*c* in accordance with one embodiment of the present disclosure. FIG. 17A illustrates an example of when a first differential voltage is created between top electrode 172 and bottom electrode 184*b* in an area of dielectric 174 that is over bottom electrode 184*b* but under exposed area 182*b*. This causes dielectric 174 to change color such that the color of dielectric 174 appears white or some contrasting color to the color of mask 180 and exposed area 182*b* can be be visible to the user. In addition, a second differential voltage is created between top electrode 172 and bottom electrodes 184*c* and 184*d* such that the color of dielectric 174 changes to appear black or to match mask 180 and exposed areas 182*c* and 182*d* may not be visible to the user and the user would not see any visible indication or very little indication or trace of exposed areas 182*c* and 182*d*.

Figure 17B:
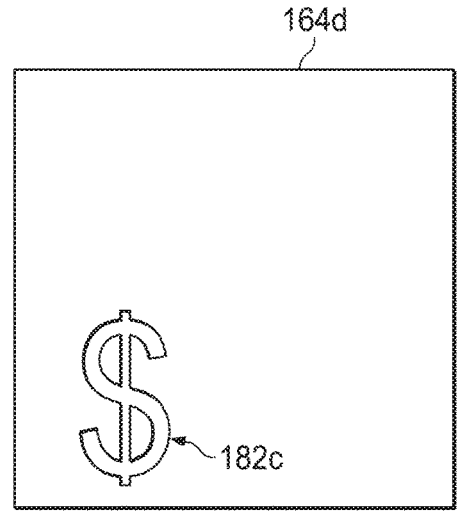
FIG. 17B is a simplified schematic diagram illustrating a block diagram view of an embodiment of a portion of a key, in accordance with one embodiment of the present disclosure.

Turning to FIG. 17B, FIG. 17B is a simplified plan view illustrating an embodiment of active element 164*d* in accordance with one embodiment of the present disclosure. FIG. 17B illustrates an example of when a first differential voltage is created between top electrode 172 and bottom electrode 184*c* in an area of dielectric 174 that is over bottom electrode 184*c* but under exposed area 182*c*. This causes dielectric 174 to change color such that the color of dielectric 174 appears white or some contrasting color to the color of mask 180 and exposed area 182*c* can be be visible to the user. In addition, a second differential voltage is created between top electrode 172 and bottom electrodes 184*b* and 184*d* such that the color of dielectric 174 changes to appear black or to match mask 180 and exposed areas 182*b* and 182*d* may not be visible to the user and the user would not see any visible indication or very little indication or trace of exposed areas 182*b* and 182*d*.

Figure 17C:
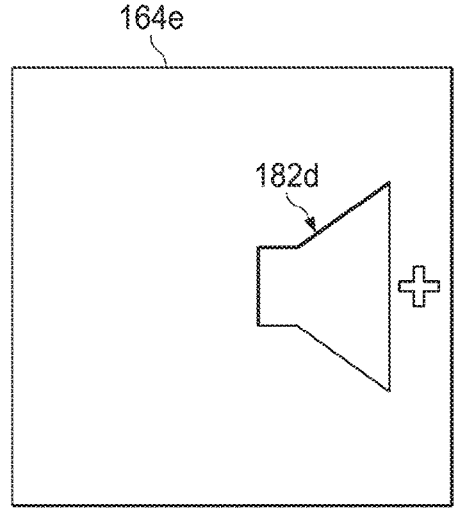
FIG. 17C is a simplified schematic diagram illustrating a block diagram view of an embodiment of a portion of a key, in accordance with one embodiment of the present disclosure.

Turning to FIG. 17C, FIG. 17C is a simplified plan view illustrating an embodiment of active element 164*e* in accordance with one embodiment of the present disclosure. FIG. 17C illustrates an example of when a first differential voltage is created between top electrode 172 and bottom electrode 184*d* in an area of dielectric 174 that is over bottom electrode 184*d* but under exposed area 182*d*. This causes dielectric 174 to change color such that the color of dielectric 174 appears white or some contrasting color to the color of mask 180 and exposed area 182*d* can be be visible to the user. In addition, a second differential voltage is created between top electrode 172 and bottom electrodes 184*b* and 184*c* such that the color of dielectric 174 changes to appear black or to match mask 180 and exposed areas 182*b* and 182*c* may not be visible to the user and the user would not see any visible indication or very little indication or trace of exposed areas 182*b* and 182*c*.

Active element 164 may be a bi-stable display. The term bi-stable refers to the ability of a display to retain content on the display even after the source of power for the display is removed. The term "segmented" refers to a form of display that is alternate to a dot matrix display, for example, as illustrated in FIGS. 16 and 17A-C. A segmented display can be built with a collection of pre-defined shapes or segments (e.g., exposed areas 182*a*-182*d*). At runtime, each segment can be driven to either a visible or a hidden state to compose a final image that can be displayed on screen. The concept of a segmented display is similar to seven segment displays used in a calculator.

Figure 18:
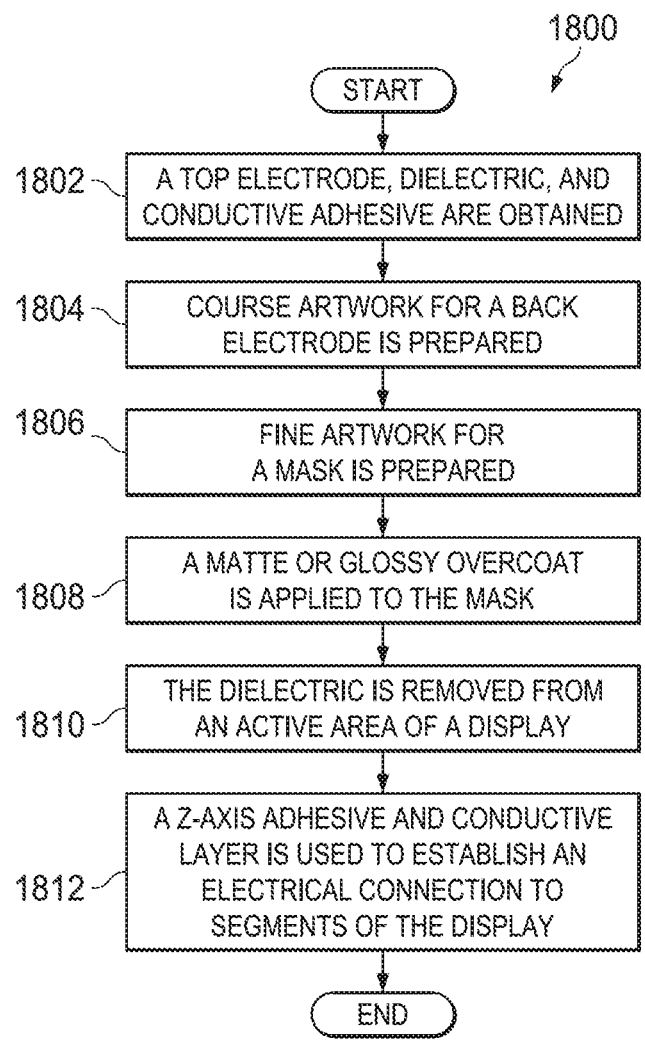
FIG. 18 is a simplified a simplified flow diagram illustrating potential operations associated with one embodiment of the present disclosure.

Turning to FIG. 18, FIG. 18 is an example flowchart illustrating possible operations of a flow 1800 that may be associated with a bi-stable display. At 1802, a colored mask is integrated on an outermost surface of a bi-stable display. At 1804, coarse artwork for a back (or bottom) electrode is prepared. For example, the back (or bottom) electrode may be base substrate 178. At 1806, fine artwork for a mask is prepared. At 1808, a matte or glossy overcoat is applied to the colored mask. At 1810, the dielectric is removed from the active area. At 1812, a z-axis adhesive and conductive layer is used in place of a tail to establish an electrical connection to segments of the bi-stable display.

Figure 19:
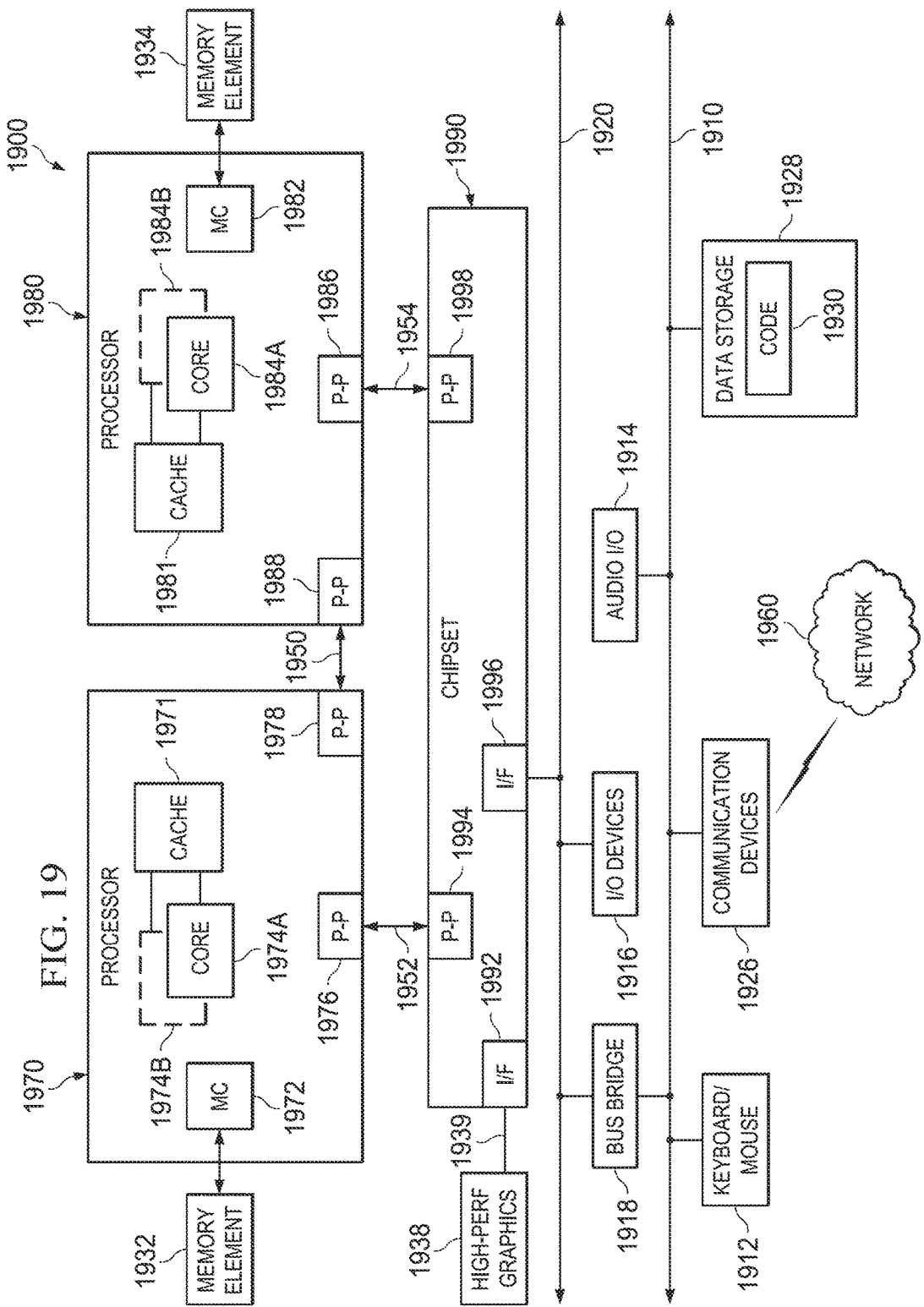
FIG. 19 is a block diagram illustrating an example computing system that is arranged in a point-to-point configuration in accordance with an embodiment.

Turning to FIG. 19, FIG. 19 illustrates a computing system 1900 that is arranged in a point-to-point (PtP) configuration according to an embodiment. In particular, FIG. 19 shows a system where processors, memory, and input/output devices are interconnected by a number of point-to-point interfaces. Generally, one or more of the network elements of electronic device 100 may be configured in the same or similar manner as computing system 1900.

As illustrated in FIG. 19, system 1900 may include several processors, of which only two, processors 1970 and 1980, are shown for clarity. While two processors 1970 and 1980 are shown, it is to be understood that an embodiment of system 1900 may also include only one such processor. Processors 1970 and 1980 may each include a set of cores (i.e., processor cores 1974A and 1974B and processor cores 1984A and 1984B) to execute multiple threads of a program. The cores may be configured to execute instruction code. Each processor 1970, 1980 may include at least one shared cache 1971, 1981. Shared caches 1971, 1981 may store data (e.g., instructions) that are utilized by one or more components of processors 1970, 1980, such as processor cores 1974 and 1984.

Processors 1970 and 1980 may also each include integrated memory controller logic (MC) 1972 and 1982 to communicate with memory elements 1932 and 1934. Memory elements 1932 and/or 1934 may store various data used by processors 1970 and 1980. In alternative embodiments, memory controller logic 1972 and 1982 may be discreet logic separate from processors 1970 and 1980.

Processors 1970 and 1980 may be any type of processor, and may exchange data via a point-to-point (PtP) interface 1950 using point-to-point interface circuits 1978 and 1988, respectively. Processors 1970 and 1980 may each exchange data with a control logic 1990 via individual point-to-point interfaces 1952 and 1954 using point-to-point interface circuits 1976, 1986, 1994, and 1998. Control logic 1990 may also exchange data with a high-performance graphics circuit 1938 via a high-performance graphics interface 1939, using an interface circuit 1992, which could be a PtP interface circuit. In alternative embodiments, any or all of the PtP links illustrated in FIG. 19 could be implemented as a multi-drop bus rather than a PtP link.

Control logic 1990 may be in communication with a bus 1920 via an interface circuit 1996. Bus 1920 may have one or more devices that communicate over it, such as a bus bridge 1918 and I/O devices 1916. Via a bus 1910, bus bridge 1918 may be in communication with other devices such as a keyboard/mouse 1912 (or other input devices such as a touch screen, trackball, etc.), communication devices 1926 (such as modems, network interface devices, or other types of communication devices that may communicate through a computer network 1960), audio I/O devices 1914, and/or a data storage device 1928. Data storage device 1928 may store code 1930, which may be executed by processors 1970 and/or 1980. In alternative embodiments, any portions of the bus architectures could be implemented with one or more PtP links.

The computer system depicted in FIG. 19 is a schematic illustration of an embodiment of a computing system that may be utilized to implement various embodiments discussed herein. It will be appreciated that various components of the system depicted in FIG. 19 may be combined in a system-on-a-chip (SoC) architecture or in any other suitable configuration. For example, embodiments disclosed herein can be incorporated into systems including mobile devices such as smart cellular telephones, tablet computers, personal digital assistants, portable gaming devices, etc. It will be appreciated that these mobile devices may be provided with SoC architectures in at least some embodiments.

Figure 20:
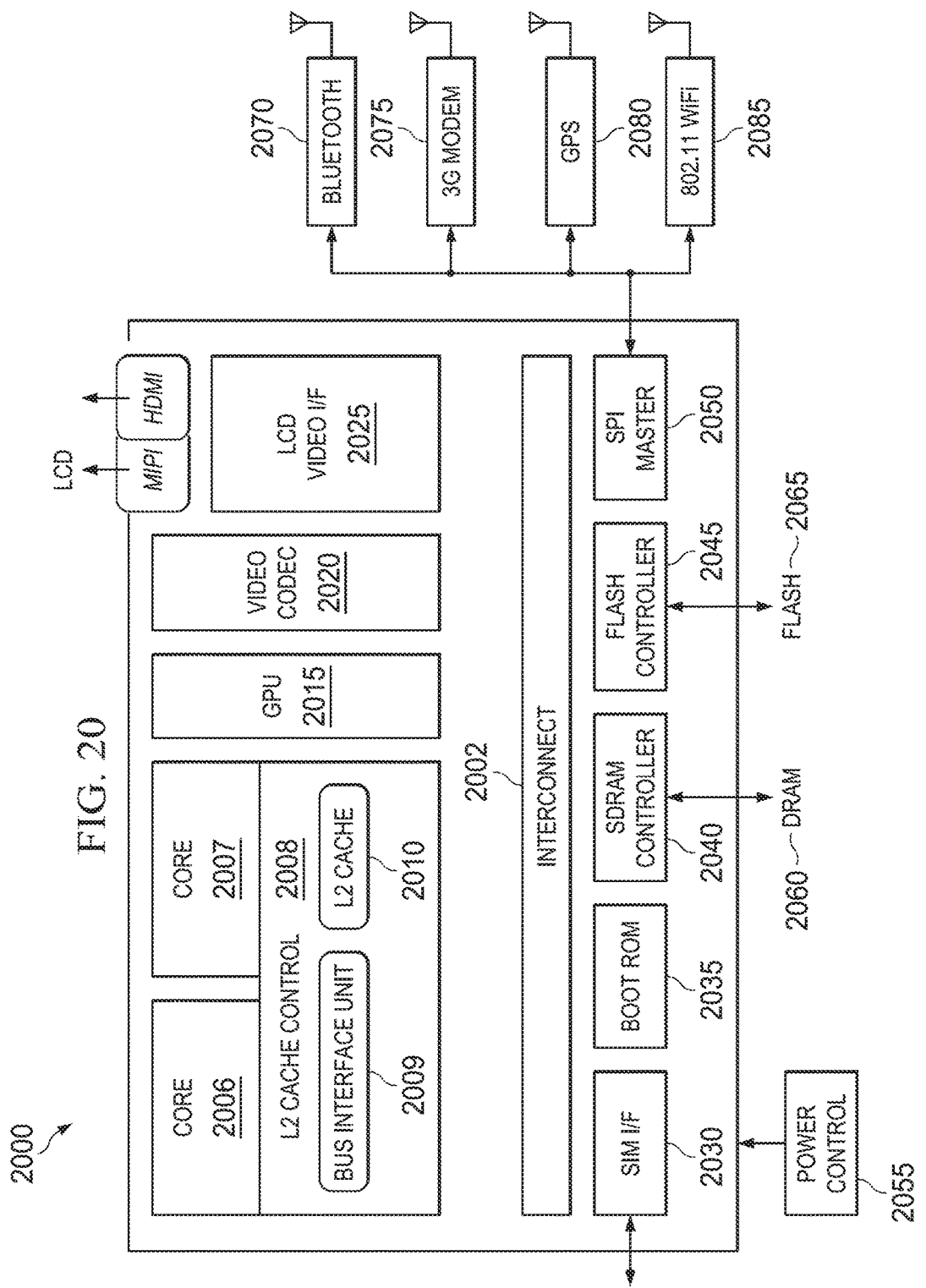
FIG. 20 is a simplified block diagram associated with an example system on chip (SOC) of the present disclosure.

Turning to FIG. 20, FIG. 20 is a simplified block diagram associated with an example SOC 2000 of the present disclosure. At least one example implementation of the present disclosure can include the keycap with an active element features discussed herein. For example, the architecture can be part of any type of tablet, smartphone (inclusive of Android™ phones, iPhones™, iPad™ Google Nexus™, Microsoft Surface™, personal computer, server, video processing components, laptop computer (inclusive of any type of notebook), Ultrabook™ system, any type of touch-enabled input device, etc.

In this example of FIG. 20, SOC 2000 may include multiple cores 2006-2007, an L2 cache control 2008, a bus interface unit 2009, an L2 cache 2010, a graphics processing unit (GPU) 2015, an interconnect 2002, a video codec 2020, and a liquid crystal display (LCD) I/F 2025, which may be associated with mobile industry processor interface (MIPI)/high-definition multimedia interface (HDMI) links that couple to an LCD.

SOC 2000 may also include a subscriber identity module (SIM) I/F 2030, a boot read-only memory (ROM) 2035, a synchronous dynamic random access memory (SDRAM) controller 2040, a flash controller 2045, a serial peripheral interface (SPI) master 2050, a suitable power control 2055, a dynamic RAM (DRAM) 2060, and flash 2065. In addition, one or more embodiments include one or more communication capabilities, interfaces, and features such as instances of Bluetooth™ 2070, a 3G modem 2075, a global positioning system (GPS) 2080, and an 802.11 Wi-Fi 2085.

In operation, the example of FIG. 20 can offer processing capabilities, along with relatively low power consumption to enable computing of various types (e.g., mobile computing, high-end digital home, servers, wireless infrastructure, etc.). In addition, such an architecture can enable any number of software applications (e.g., Android™, Adobe™ Flash™ Player, Java Platform Standard Edition (Java SE), JavaFX, Linux, Microsoft Windows Embedded, Symbian and Ubuntu, etc.). In at least one embodiment, the core processor may implement an out-of-order superscalar pipeline with a coupled low-latency level-2 cache.

Figure 21:
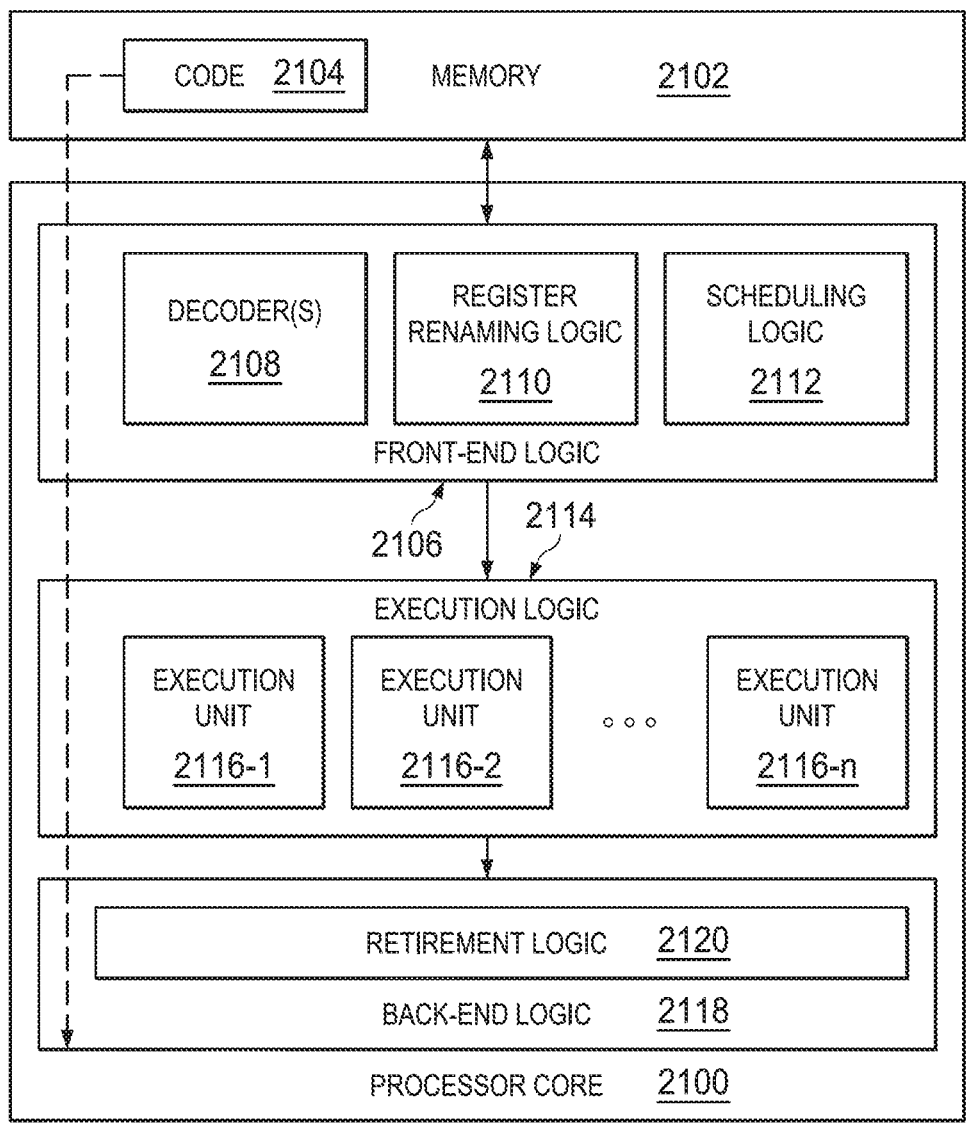
FIG. 21 is a block diagram illustrating an example processor core, in accordance with an embodiment.

FIG. 21 illustrates a processor core 2100 according to an embodiment. Processor core 21 may be the core for any type of processor, such as a micro-processor, an embedded processor, a digital signal processor (DSP), a network processor, or other device to execute code. Although only one processor core 2100 is illustrated in FIG. 21, a processor may alternatively include more than one of the processor core 2100 illustrated in FIG. 21. For example, processor core 2100 represents an embodiment of processors cores 1974a, 1974b, 1984a, and 1984b shown and described with reference to processors 1970 and 1980 of FIG. 19. Processor core 2100 may be a single-threaded core or, for at least one embodiment, processor core 2100 may be multithreaded in that it may include more than one hardware thread context (or "logical processor") per core.

FIG. 21 also illustrates a memory 2102 coupled to processor core 2100 in accordance with an embodiment. Memory 2102 may be any of a wide variety of memories (including various layers of memory hierarchy) as are known or otherwise available to those of skill in the art. Memory 2102 may include code 2104, which may be one or more instructions, to be executed by processor core 2100. Processor core 2100 can follow a program sequence of instructions indicated by code 2104. Each instruction enters a front-end logic 2106 and is processed by one or more decoders 2108. The decoder may generate, as its output, a micro operation such as a fixed width micro operation in a predefined format, or may generate other instructions, microinstructions, or control signals that reflect the original code instruction. Front-end logic 2106 also includes register renaming logic 2110 and scheduling logic 2112, which generally allocate resources and queue the operation corresponding to the instruction for execution.

Processor core 2100 can also include execution logic 2114 having a set of execution units 2116-1 through 2116-N. Some embodiments may include a number of execution units dedicated to specific functions or sets of functions. Other embodiments may include only one execution unit or one execution unit that can perform a particular function. Execution logic 2114 performs the operations specified by code instructions.

After completion of execution of the operations specified by the code instructions, back-end logic 2118 can retire the instructions of code 2104. In one embodiment, processor core 2100 allows out of order execution but requires in order retirement of instructions. Retirement logic 2120 may take a variety of known forms (e.g., re-order buffers or the like). In this manner, processor core 2100 is transformed during execution of code 2104, at least in terms of the output generated by the decoder, hardware registers and tables utilized by register renaming logic 2110, and any registers (not shown) modified by execution logic 2114.

Although not illustrated in FIG. 21, a processor may include other elements on a chip with processor core 2100, at least some of which were shown and described herein with reference to FIG. 19. For example, as shown in FIG. 19, a processor may include memory control logic along with processor core 2100. The processor may include I/O control logic and/or may include I/O control logic integrated with memory control logic.

It is imperative to note that all of the specifications, dimensions, and relationships outlined herein (e.g., height, width, length, materials, etc.) have only been offered for purposes of example and teaching only. Each of these data may be varied considerably without departing from the spirit of the present disclosure, or the scope of the appended claims. The specifications apply only to one non-limiting example and, accordingly, they should be construed as such. In the foregoing description, example embodiments have been described. Various modifications and changes may be made to such embodiments without departing from the scope of the appended claims. The description and drawings are, accordingly, to be regarded in an illustrative rather than a restrictive sense.

Although the present disclosure has been described in detail with reference to particular arrangements and configurations, these example configurations and arrangements may be changed significantly without departing from the scope of the present disclosure. Moreover, certain components may be combined, separated, eliminated, or added based on particular needs and implementations. Additionally, although the present disclosure has been illustrated with reference to particular elements and operations that facilitate the communication process, these elements and operations may be replaced by any suitable architecture, protocols, and/or processes that achieve the intended functionality of the present disclosure.

Numerous other changes, substitutions, variations, alterations, and modifications may be ascertained to one skilled in the art and it is intended that the present disclosure encompass all such changes, substitutions, variations, alterations, and modifications as falling within the scope of the appended claims. In order to assist the United States Patent and Trademark Office (USPTO) and, additionally, any readers of any patent issued on this application in interpreting the claims appended hereto, Applicant wishes to note that the Applicant: (a) does not intend any of the appended claims to invoke paragraph six (6) of 35 U.S.C. section 112 as it exists on the date of the filing hereof unless the words "means for" or "step for" are specifically used in the particular claims; and (b) does not intend, by any statement in the specification, to limit this disclosure in any way that is not otherwise reflected in the appended claims.

OTHER NOTES AND EXAMPLES

Example A1 is a display including a mask that includes a one or more exposed areas, a top electrode, one or more bottom electrodes, a dielectric between the top electrode and the one or more bottom electrodes, and an electrical connection to create a differential voltage between the top electrode and the one or more bottom electrodes.

In Example A2, the subject matter of Example A1 can optionally include where a color of the dialectic material changes when a differential voltage is applied.

In Example A3, the subject matter of any one of Examples A1-A2 can optionally include where the display is a bi-stable display.

In Example A4, the subject matter of any one of Examples A1-A3 can optionally include where a thickness of the mask, top electrode, one or more bottom electrodes, and dielectric is less than about three (3) millimeters.

In Example A5, the subject matter of any one of Examples A1-A4 can optionally include where the electrical connection is within an active area.

In Example A6, the subject matter of any one of Examples A1-A5 can optionally include where each of the one or more bottom electrodes corresponds to an exposed area from the one or more exposed areas.

In Example A7, the subject matter of any one of Example A1-A6 can optionally include where each of the one or more bottom electrodes is associated with an exposed area and a visibility of each one or more exposed areas is independently controlled by creating a differential voltage between the top electrode and each of the one or more bottom electrodes.

Example M1 is a method including creating a display, where the display includes a mask that includes a one or more exposed areas, a top electrode, one or more bottom electrodes, a dielectric between the top electrode and the one or more bottom electrodes, and an electrical connection to create a differential voltage between the top electrode and the one or more bottom electrodes.

In Example M2, the subject matter of Example M1 can optionally include where a color of the dialectic material changes when a differential voltage is applied.

In Example M3, the subject matter of any one of the Examples M1-M2 can optionally include where the display is a bi-stable display.

In Example M4, the subject matter of any one of the Examples M1-M3 can optionally include where a thickness of the mask, top electrode, one or more bottom electrodes, and dielectric is less than about three (3) millimeters.

In Example M5, the subject matter of any one of the Examples M1-M4 can optionally include where the electrical connection is within an active area.

In Example M6, the subject matter of any one of the Examples M1-M5 can optionally include where each of the one or more bottom electrodes corresponds to an exposed area from the one or more exposed areas.

In Example AA1, an electronic device can include a first housing, where the first housing includes a keyboard. The keyboard includes keys and each key includes a keycap, where at least a portion of each keycap includes a mask that includes a one or more exposed areas, a top electrode, one or more bottom electrodes, a dielectric between the top electrode and the one or more bottom electrodes, and an electrical connection to create a differential voltage between the top electrode and the one or more bottom electrodes.

In Example, AA2, the subject matter of Example AA1 can optionally include where a color of the dialectic material changes when a differential voltage is applied.

In Example AA3, the subject matter of any one of Examples AA1-AA2 can optionally include where the display is a bi-stable display.

In Example AA4, the subject matter of any one of Examples AA1-AA3 can optionally include where a thickness of the mask, top electrode, one or more bottom electrodes, and dielectric is less than about three (3) millimeters.

In Example AA5, the subject matter of any one of Examples AA1-AA4 can optionally include where the electrical connection is within an active area.

In Example AA6, the subject matter of any one of Examples AA1-AA5 can optionally include where each of the one or more bottom electrodes corresponds to an exposed area from the one or more exposed areas.

In Example AA7, the subject matter of any one of Examples AA1-AA6 can optionally include where each of the one or more bottom electrodes is associated with an exposed area and a visibility of each one or more exposed areas is independently controlled by creating a differential voltage between the top electrode and each of the one or more bottom electrodes.

Example X1 is a machine-readable storage medium including machine-readable instructions to implement a method or realize an apparatus as in any one of the Examples A1-A7, or M1-M7. Example Y1 is an apparatus comprising means for performing of any of the Example methods M1-M7. In Example Y2, the subject matter of Example Y1 can optionally include the means for performing the method comprising a processor and a memory. In Example Y3, the subject matter of Example Y2 can optionally include the memory comprising machine-readable instructions.

The invention claimed is:

1. A bi-stable display in a keycap of a key, the bi-stable display comprising:
    a mask that includes a one or more exposed areas;
    a top electrode;
    one or more bottom electrodes;
    a dielectric between the top electrode and the one or more bottom electrodes, wherein the dielectric changes from one state to another state when a differential voltage is applied between the top electrode and the one or more bottom electrodes; and
    an electrical connection to create the differential voltage between the top electrode and the one or more bottom electrodes, wherein the bi-stable display is above a dome of the key.

2. The bi-stable display of claim 1, wherein a color of the dielectric changes when the differential voltage is applied between the top electrode and the one or more bottom electrodes.

3. The bi-stable display of claim 1, wherein a thickness of the mask, top electrode, one or more bottom electrodes, and dielectric is less than about three (3) millimeters.

4. The bi-stable display of claim 1, wherein the electrical connection is within an active area.

5. The bi-stable display of claim 1, wherein each of the one or more bottom electrodes corresponds to an exposed area from the one or more exposed areas.

6. The bi-stable display of claim 1, wherein each of the one or more bottom electrodes is associated with an exposed area and a visibility of each one or more exposed areas is independently controlled by creating an associated differential voltage between the top electrode and each of the one or more bottom electrodes.

7. The bi-stable display of claim 1, wherein an image on the keycap is visible to a user when the dielectric is in a first state but is not visible to the user when the dielectric is in a second state.

8. A method comprising:
    creating a bi-stable display in a keycap of a key, wherein the bi-stable display includes:
    a mask that includes a one or more exposed areas;
    a top electrode;
    one or more bottom electrodes;
    a dielectric between the top electrode and the one or more bottom electrodes, wherein the dielectric changes from one state to another state when a differential voltage is applied between the top electrode and the one or more bottom electrodes; and
    an electrical connection to create the differential voltage between the top electrode and the one or more bottom electrodes, wherein the bi-stable display is above a dome of the key.

9. The method of claim 8, wherein a color of the dielectric changes when the differential voltage is applied between the top electrode and the one or more bottom electrodes.

10. The method of claim 8, wherein a thickness of the mask, top electrode, one or more bottom electrodes, and dielectric is less than about three (3) millimeters.

11. The method of claim 8, wherein the electrical connection is within an active area.

12. The method of claim 8, wherein each of the one or more bottom electrodes corresponds to an exposed area from the one or more exposed areas.

13. An electronic device, comprising:
    a first housing, wherein the first housing includes a keyboard, wherein the keyboard includes a plurality of keys and each of the plurality of keys includes a keycap above a dome, wherein each of the plurality of keys includes a bi-stable display in the keycap above the dome, wherein the bi-stable display includes:

a mask that includes a one or more exposed areas;
a top electrode;
one or more bottom electrodes;
a dielectric between the top electrode and the one or more bottom electrodes, wherein the dielectric changes from one state to another state when a differential voltage is applied between the top electrode and the one or more bottom electrodes; and
an electrical connection to create the differential voltage between the top electrode and the one or more bottom electrodes, wherein the display is above the dome of the key.

14. The electronic device of claim 13, wherein a color of the dielectric changes when the differential voltage is applied between the top electrode and the one or more bottom electrodes.

15. The electronic device of claim 13, wherein a thickness of the mask, top electrode, one or more bottom electrodes, and dielectric is less than about three (3) millimeters.

16. The electronic device of claim 15, wherein the electrical connection is within an active area.

17. The electronic device of claim 13, wherein each of the one or more bottom electrodes corresponds to an exposed area from the one or more exposed areas.

18. The electronic device of claim 13, wherein each of the one or more bottom electrodes is associated with an exposed area and a visibility of each one or more exposed areas is independently controlled by creating an associated differential voltage between the top electrode and each of the one or more bottom electrodes.

* * * * *